US006287790B1

(12) United States Patent
Lelièvre et al.

(10) Patent No.: US 6,287,790 B1
(45) **Date of Patent: *Sep. 11, 2001**

(54) UTILIZATION OF NUCLEAR STRUCTURAL PROTEINS FOR TARGETED THERAPY AND DETECTION OF PROLIFERATIVE AND DIFFERENTIATION DISORDERS

(75) Inventors: Sophie Lelièvre; Mina Bissell, both of Berkeley, CA (US)

(73) Assignee: The Regents of the University of California, Oakland, CA (US)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/452,294

(22) Filed: Nov. 30, 1999

Related U.S. Application Data

(60) Provisional application No. 60/110,420, filed on Nov. 30, 1998.

(51) Int. Cl.[7] .......................... G01N 33/574; G01N 33/53; G01N 33/567; G01N 33/58

(52) U.S. Cl. .......................... 435/7.23; 435/7.1; 435/7.2; 436/64

(58) Field of Search .......................... 435/7.1, 7.23, 435/7.2; 436/64

(56) References Cited

U.S. PATENT DOCUMENTS 5,686,562 * 11/1997 Toukatly et al. .................... 530/324

OTHER PUBLICATIONS

Skog et al., Fundamentals of Analytical Chemistry, pp. 19, 22, and 506, 1988.*

Willard et al., Instrumental Method of Analysis, page 518, 1988.*

Lelievre, et al., The Extracellular matrix differentially modulates the distribution of nuclear mitotic apparatus protein in non–malignant and malignant HMT–3522 Mammary Epithelial Cells, A Culture Model of Progressive Human Breast Cancer, Molecular Biolo, 1996.*

Gobert et al., Ultrastructural localization of NuMA withing WCF–7 cells, a human breast cancer line, Molecular Biology of the Cell, vol. 9, page 445A, Nov. 1998.*

Compton et al., The Journal of Cell Biology, vol. 116(6), pp. 1395–1408, 1996.*

Bjorn K. Lydersen, "Human–Specific Nuclear Protein That Associates with the Polar Region of the Mitotic Apparatus: Distribution in a Human/Hamster Hybrid Cell," Cell, pp. 489–499, (Nov. 17, 1980).

Valerie Weaver, "Degradation of nuclear matrix and DNA cleavage in apoptotic thymocytes," Journal of Cell Science, The Company of Biologists Limited (Great Britain), vol. 109 (No. 1), pp. 45–56, (Jul. 17, 1996).

Dacheng He, "Core Filaments of the Nuclear Matrix," Journal of Cell Biology, The Rockefeller University Press (USA), pp. 569–580, (Mar. 17, 1990).

* cited by examiner

*Primary Examiner*—Anthony C. Caputa
*Assistant Examiner*—Jennifer Hunt
(74) *Attorney, Agent, or Firm*—Charles R. Nold; David J. Aston

(57) ABSTRACT

The localization of nuclear apparatus proteins (NUMA) is used to identify tumor cells and different stages in the tumor progression and differentiation processes. There is a characteristic organization of NuMA in tumor cells and in phenotypically normal cells. NuMA distribution patterns are significantly less diffuse in proliferating non-malignant cells compared to malignant cells. The technique encompasses cell immunostaining using a NuMA specific antibody, and microscopic analysis of NuMA distribution within each nucleus.

4 Claims, 17 Drawing Sheets

(10 of 17 Drawing Sheet(s) Filed in Color)

Dynamics of the distribution of NM proteins in 3D rBM (Only the cell nucleus is represented, NuMA in red; Rb and SRm160 in green)

Nuclear Distribution Pattern of NUMA Protein Depends on Growth Status in Human Mammary Epithelial Cells 2D Culture, on Plastic Normalized Contrast of Blurred NUMA Pattern Proliferating Non-Malignant and Malignant Mammary Epithelial Cells Show Significantly Different Nuclear Distribution of NUMA Protein 2D Culture, on Plastic Normalized Contrast of Blurred NUMA Pattern

| | | |
|---|---|---|
| Ki67 | (+) | (+) |
| n | 229 | 84 |

**NuMA staining
(3D culture-day 4)**

Measure of the sharpness of NuMA staining pattern using blur factor 4 immunogold labeling of NuMA in situ cell matrix preparation (Only the cell nucleus is represented,
NuMA distribution pattern is in red)

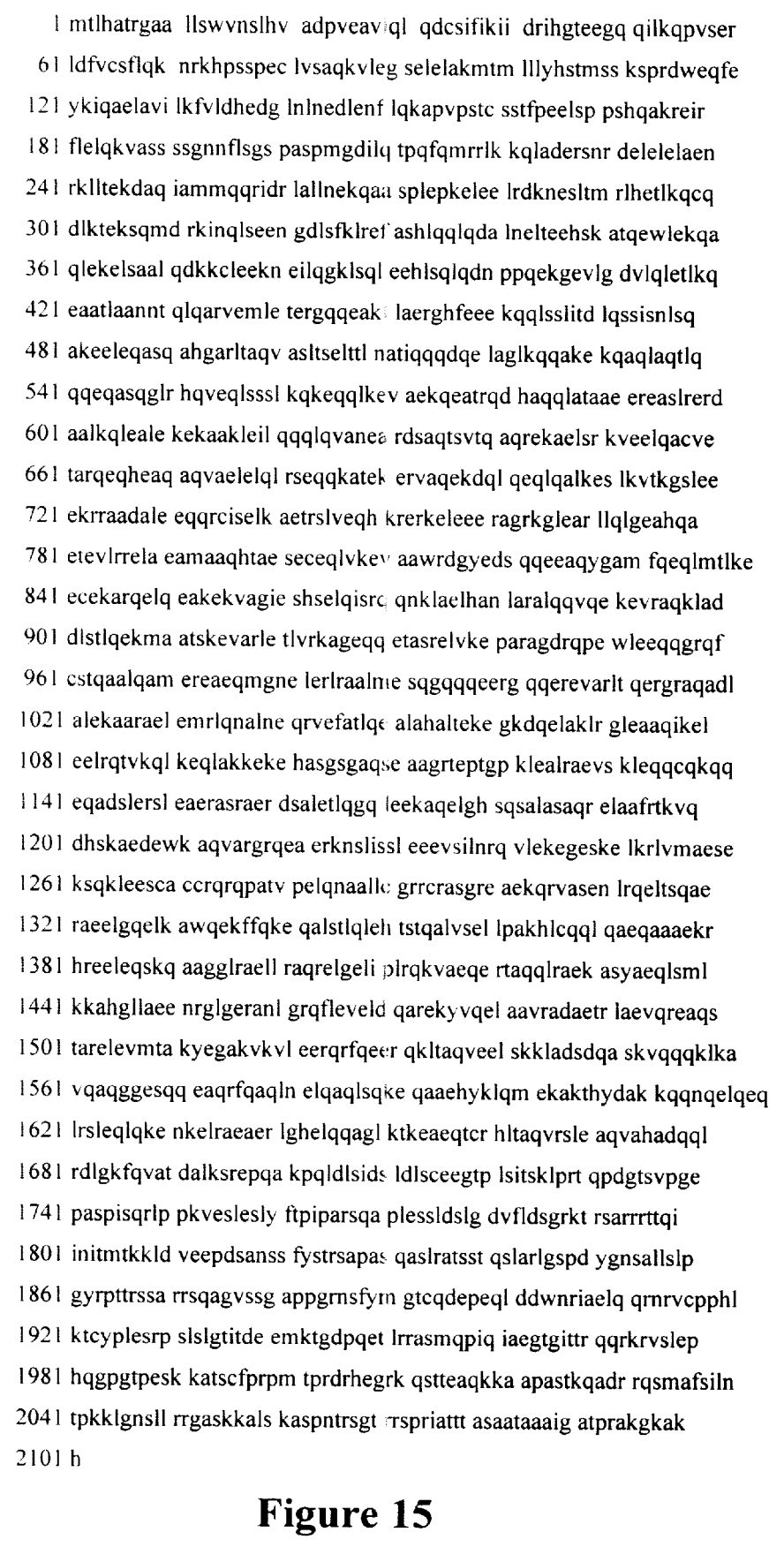

1 mtlhatrgaa llswvnslhv adpveaviql qdcsifikii drihgteegq qilkqpvser
61 ldfvcsflqk nrkhpsspec lvsaqkvleg selelakmtm lllyhstmss ksprdweqfe
121 ykiqaelavi lkfvldhedg lnlnedlenf lqkapvpstc sstfpeelsp pshqakreir
181 flelqkvass ssgnnflsgs paspmgdilq tpqfqmrrlk kqladersnr delelelaen
241 rklltekdaq iammqqridr lallnekqaa splepkelee lrdknesltm rlhetlkqcq
301 dlkteksqmd rkinqlseen gdlsfklref ashlqqlqda lnelteehsk atqewlekqa
361 qlekelsaal qdkkcleekn eilqgklsql eehlsqlqdn ppqekgevlg dvlqletlkq
421 eaatlaannt qlqarvemle tergqqeak laerghfeee kqqlsslitd lqssisnlsq
481 akeeleqasq ahgarltaqv asltselttl natiqqqdqe laglkqqake kqaqlaqtlq
541 qqeqasqglr hqveqlsssl kqkeqqlkev aekqeatrqd haqqlataae ereaslrerd
601 aalkqleale kekaakleil qqqlqvanea rdsaqtsvtq aqrekaelsr kveelqacve
661 tarqeqheaq aqvaelelql rseqqkatek ervaqekdql qeqlqalkes lkvtkgslee
721 ekrraadale eqqrciselk aetrslveqh krerkeleee ragrkglear llqlgeahqa
781 etevlrrela eamaaqhtae seceqlvkev aawrdgyeds qqeeaqygam fqeqlmtlke
841 ecekarqelq eakekvagie shselqisrq qnklaelhan laralqqvqe kevraqklad
901 dlstlqekma atskevarle tlvrkageqq etasrelvke paragdrqpe wleeqqgrqf
961 cstqaalqam ereaeqmgne lerlraalme sqgqqqeerg qqerevarlt qergraqadl
1021 alekaarael emrlqnalne qrvefatlqe alahalteke gkdqelaklr gleaaqikel
1081 eelrqtvkql keqlakkeke hasgsgaqse aagrteptgp klealraevs kleqqcqkqq
1141 eqadslersl eaerasraer dsaletlqgq leekaqelgh sqsalasaqr elaafrtkvq
1201 dhskaedewk aqvargrqea erknslissl eeevsilnrq vlekegeske lkrlvmaese
1261 ksqkleesca ccrqrqpatv pelqnaallc grrcrasgre aekqrvasen lrqeltsqae
1321 raeelgqelk awqekffqke qalstlqleh tstqalvsel lpakhlcqql qaeqaaaekr
1381 hreeleqskq aagglraell raqrelgeli plrqkvaeqe rtaqqlraek asyaeqlsml
1441 kkahgllaee nrglgeranl grqfleveld qarekyvqel aavradaetr laevqreaqs
1501 tarelevmta kyegakvkvl eerqrfqeer qkltaqveel skkladsdqa skvqqqklka
1561 vqaqggesqq eaqrfqaqln elqaqlsqke qaaehyklqm ekakthydak kqqnqelqeq
1621 lrsleqlqke nkelraeaer lghelqqagl ktkeaeqtcr hltaqvrsle aqvahadqql
1681 rdlgkfqvat dalksrepqa kpqldlsids ldlsceegtp lsitsklprt qpdgtsvpge
1741 paspisqrlp pkveslesly ftpiparsqa plessldslg dvfldsgrkt rsarrrttqi
1801 initmtkkld veepdsanss fystrsapas qaslratsst qslarlgspd ygnsallslp
1861 gyrpttrssa rrsqagvssg appgrnsfym gtcqdepeql ddwnriaelq qrnrvcpphl
1921 ktcyplesrp slslgtitde emktgdpqet lrrasmqpiq iaegtgittr qqrkrvslep
1981 hqgpgtpesk katscfprpm tprdrhegrk qstteaqkka apastkqadr rqsmafsiln
2041 tpkklgnsll rrgaskkals kaspntrsgt trspriattt asaataaaig atprakgkak
2101 h

Figure 15

UTILIZATION OF NUCLEAR STRUCTURAL PROTEINS FOR TARGETED THERAPY AND DETECTION OF PROLIFERATIVE AND DIFFERENTIATION DISORDERS

REFERENCE TO RELATED APPLICATIONS

This application claims priority benefit of U.S. provisional application Ser. No. 60/110,420, filed Nov. 30, 1998, now abandoned, which is hereby incorporated herein by reference in its entirety.

STATEMENT REGARDING FEDERAL SPONSORSHIP

This invention was made with U.S. Government support under Contract No. DE -AC03-76SF0098 between the U.S. Department of Energy and the University of California for the operation of Lawrence Berkeley National Laboratory (LBNL). The U. S. Government may have certain rights to this invention.

FIELD OF THE INVENTION

The present invention relates to the use of nuclear structural proteins, particularly NuMA (Nuclear Mitotic Apparatus Protein) as: a diagnostic indicator of cell phenotype in histopathology; a transporter protein, to which therapeutic agents of interest may be linked for delivery to the nucleus; and a drug discovery target for agents that block or mimic the interaction between NuMA and its binding partners.

BACKGROUND OF THE INVENTION

Abbreviations: CMS protein, connective membrane skeleton protein; FA, focal adhesion; NLS, nuclear localization signal; NES, nuclear export signal. NM, nuclear matrix; rBM, reconstituted basement membrane; HMEC, human mammary epithelial cells; 2D and 3D, two and three dimensional; Rb, retinoblastoma protein; ECM, extracellular matrix; EGF, epidermal growth factor; mAb, monoclonal antibody;

The cell nucleus is organized by a non-chromatin internal structure referred to as the nuclear matrix (NM). Identified NM components include coiled-coil proteins, cell cycle regulators, tissue-specific transcription factors, and RNA splicing factors. Although splicing factors have been shown to redistribute during cellular differentiation, and following the induction of gene expression, such alterations in nuclear organization, defined here as the spatial distribution of nuclear components, are thought to be the consequence of changes in gene expression. However, both NM composition and structure may affect gene expression and cellular function, and thus a systematic analysis of nuclear organization during such a complex process as tissue differentiation is warranted.

To study the effect of cell growth and tissue differentiation on nuclear organization, we have used a reconstituted basement membrane (rBM)-directed model of mammary gland morphogenesis. The HMT-3522 human mammary epithelial cells (HMECs) were isolated from reduction mammoplasty and became immortalized in culture. When embedded within a rBM, these cells growth arrest, organize an endogenous BM and form polarized acinus-like structures with vectorial secretion of sialomucin into a central lumen. Using this model, we have compared the nuclear organization of HMECs cultured on a plastic surface (2D monolayer) vs. a 3-dimensional (3D) rBM. Nuclear organization was assessed by examining the distribution of the coiled-coil NM proteins lamin B and NuMA, the cell cycle regulator Rb (p110Rb; 5), and the splicing factor SRm 160 (formerly known as B 1 C8; 16). These proteins had distinct spatial distribution patterns specific for proliferation, growth-arrest and acini formation. Moreover, disruption of nuclear organization in acini by either perturbing histone acetylation, or directly modifying the distribution of NuMA proteins, altered the acinar phenotype.

We have previously determined that the extracellular matrix (ECM) directs morphogenesis and gene expression in mammary epithelial cells. Here we show that a reciprocal relationship exists between the ECM and nuclear organization. These findings underscore a role for nuclear organization in regulation of gene expression and provide a possible framework for how cell-ECM interactions determine cell and tissue phenotype.

Structure Of NuMA Proteins Used Herein

Nuclear Mitotic Apparatus protein (NuMA) is a 238-kDa protein of the nuclear matrix in interphase that relocates to the spindle poles in mitosis. The globular tail domain (residues 1701 to 2115) contains the nuclear targeting sequence, the site for binding to the mitotic spindle as well as a site responsible for nuclear reformation. In the full-length NuMA molecule, point mutations at position 1988 or 1989 or a double mutation at residues 2004 and 2005 cause NuMA to accumulate in the cytoplasm of both BHK and HeLa cells. It is believed that a bipartite nuclear location signal involving the sequences RKR (1987–1989) and KK (2004–2005) which are separated by 14 amino acid residues is necessary for translocation of NuMA from the cytoplasm. Observation of micronuclei formation suggests that a region important for normal nuclear reformation lies in the C-terminal 130 residues. Finally, NuMA mutant proteins ending at or after residue 1800 bind to the spindle poles of mitotic cells, while NuMA proteins ending at or before residue 1750 do not. The NuMA protein further contains phosphorylation sites. Mutation of the predicted p34cdc2 phosphorylation sites in NuMA impairs the assembly of the mitotic spindle and blocks mitosis. A preferred sequence for NuMA is taken from EMBL GenBank DDBJ: Assession Number Z11584, and is shown in SEQ.ID. No. 1.

SUMMARY OF THE INVNTION

Using a 3D model of human mammary epithelial cell culture, we have shown that the distribution of the structural protein NuMA within the nucleus depends on the cell status, and that the distribution of NuMA into enlarged peripheral foci observed in acini-like structures (characteristic of normal breast tissue) plays a role in maintaining acini phenotype and the state of chromatin organization.

We can disrupt NuMA distribution by introducing antibodies directed against part of the sequence of the protein in living cells (after acini formation) and subsequently alter cell and tissue phenotype. Such phenomenon was not reproduced in breast tumor cells in which NuMA is diffusely distributed in the nucleus.

We also have data showing that NuMA shuttles between nuclear sites and cytoplasmic sites. The fact that NuMA is found associated with the cell skeleton in both the cytoplasm (cytoskeleton) and the nucleus (nuclear matrix- the non chromatin structure of the nucleus) suggests this protein is an anchor protein which may participate in signal transduction by shuttling between specific sites in the cell and initiating cellular functions by itself or via the tethering of other proteins.

These data enable us to conceive and reduce to practice the following methods for utilizing the supramolecular organization of nuclear proteins for detection and treatment of pathologies.

1) Relocalization of nuclear proteins inside the nucleus may be used as a read-out to identify cell phenotype in histopathology.

It has been shown that localization of proteins within a tissue depends on the stage of development and differentiation (shown for extracellular matrix proteins, cell adhesion complex-associated proteins, retinoic acid receptor, topoisomerase II). Moreover variation in protein localization inside a tissue is often associated with changes in expression of the protein. Our work has demonstrated that the distribution of proteins also varies within the nucleus of cells that are part of a morphogenesis and differentiation process and that, in this case, the change in distribution is not associated with an alteration in the level of protein expression. A few examples of redistribution of nuclear proteins were already described in the literature, but none had demonstrated a clear relationship between the progressive relocalization of nuclear proteins and a morphogenic and differentiation process including proliferation, growth-arrest and complete morphogenesis of acini. We have also shown that there is a characteristic organization of NuMA in breast tumor cells and that NuMA organization in revertant cells mimics the organization observed in phenotypically normal cells (-cells arranged into acini).

According to the present invention, the localization of nuclear structural proteins such as NuMA is used to identify tumors cells (starting with mammary tissue) and different stages in the tumor progression and differentiation processes. The technique encompasses immunostaining of cell culture and tissue sections obtained from reduction tissueplasty.

We have shown that the nuclear mitotic apparatus protein (NuMA) redistributes within the nucleus of non-malignant mammary epithelial cells undergoing acinar morphogenesis in a three-dimensional (3D) system of culture. Notably, proliferation, mitotic phase, growth-arrest, and formation of breast glandular structures (acini) are characterized by a different nuclear localization of NuMA. Following differentiation into acini, NuMA is distributed into enlarged foci-like structures at the periphery of the nuclei. This pattern is also found in the acini of resting human mammary gland (staining on tissue sections) which indicates that the distribution of NuMA seen in acini recapitulated in 3D cultures is physiologically relevant.

Using the same manipulatable system of 3D cell culture, we have now shown that if acinar morphogenesis is prevented in S1 cells by overexpressing the epidermal growth-factor receptor, NuMA fails to organize into enlarged peripheral foci within the nucleus. Moreover NuMA distribution is profoundly altered in the nuclei of malignant mammary epithelial T4-2 cells organized in tumor-like clusters compared to non-malignant S1-50 cells which have undergone acinar morphogenesis (example 4). When T4-2 cells are induced to phenotypically revert and form acini using beta-I integrin or tyrphostin treatment, NuMA distribution becomes similar to what was observed in acinar S1-50 cells (example 5). These results confirm that NuMA is a marker of different cellular phenotypes and its distribution can be use to distinguish, using a simple staining procedure, cells which have undergone acinar differentiation from non-differentiated cells. We can also discriminate between proliferating (non-differentiated) non-malignant and malignant cells following immunostaining against NuMA, using a punctateness algorithm. Simple microscopic observation shows that NuMA distribution appears similarly diffuse in proliferating non-malignant and malignant cells. Moreover, both these types of cells show similar distribution and/or expression patterns of classical parameters of proliferation Rb, Ki67, PCNA, and cyclin D1. Nevertheless, by applying an algorithm that permits the mathematical analysis of staining pattern punctateness, we were able to determine that NuMA distribution patterns are significantly more punctate (or less diffuse) in proliferating non-malignant cells compared to malignant cells (Example 6). These results could be obtained for cells cultured as monolayer on plastic surfaces as well as in 3D. Hence the analysis of NuMA distribution may enable investigators to discriminate between proliferative disorders involving non-malignant cells and malignant proliferative disorders like cancers.

2) The identification of functional sequences of a nuclear matrix protein, the localization of which depends on the cell status and which shuttles between the cytoplasm and the nucleus, enables the development of new models of targeted therapvy.

a) Use of NuMA properties (and proteins behaving similarly) to transport functional proteins or drugs to specific locations inside the cells.

Although predominantly located in the nucleus, the nuclear matrix protein NuMA can be found associated with cytoplasmic structures (e.g., cytoskeleton fibers) and membrane skeleton structures. This was demonstrated by preparing nuclear matrices in which soluble proteins and DNA are removed. The fact that NuMA is found attached to the cell skeleton suggests it may be an anchor protein.

Anchor proteins have been defined as proteins that tether other proteins to the cell skeleton, and therefore may be involved in controlling biological processes by for instance creating target loci for reception of signals or concentrating a "molecular reaction or process" to specific locations. It has been shown that the same anchor protein can be found in multicompartments within the cell and thus may participate in the regulation of cell processes by directing retention of proteins (e.g.: a specific type of kinase) in a cell compartment compared to another compartment. Finally it has also been shown that motor proteins can use anchor proteins for their motility.

Interestingly, we have observed that NuMA is found in different locations in the nucleus depending on cell status, and it is also found associated with cytoplasmic sites. Although several proteins that bind NuMA still have to be identified, it has been shown that splicing factors can co-immunoprecipitate with NuMA and that NuMA binds to the motor protein dynein during mitosis and protein band 4.1 in the nucleus. Our computational search also suggests that NuMA may interact with actin and histones.

The capacity for NuMA to be anchored in different cell sites may be used to bring molecules of interest to target sites or loci inside the cell. Moreover the fact that NuMA shuttles between the cytoplasm and the nucleus suggests it may be used to bring other molecules inside the nucleus. For instance, we have shown that NuMA localization is restricted to interchromatin granules (-where RNA splicing factors are concentrated) in mammary epithelial cells that have undergone morphogenesis and differentiation (in non-malignant cells and revertant cells). The determination of the sequence of NuMA protein that is responsible for targeting and anchoring the protein to interchromatin granules may lead to the development of targeted differentiation therapy of tumor cells in which NuMA is usually found diffusely distributed in the nucleus. This may be achieved by preparing fusion proteins containing the sequence of NuMA that targets and anchors it to the interchromatin granules and the sequence necessary for entering the nucleus (nuclear localization signal) and another sequence of a protein or a full length protein that would induce specific biochemical reactions at the target site that would subsequently revert the tumor phenotype by for instance altering gene expression (-interchromatin granules are part of the transcriptional machinery inside the nucleus). The non-NuMA part of the fusion protein could also be an inhibitor of nuclear function that would lead to the death of tumor cells. Fusion proteins could also be used to correct proliferative or differentiation disorders different from cancers.

Similarly, the identification of the NuMA sequence responsible for its attachment to cytoplasmic structures may be used to create fusion proteins containing this targeting sequence but devoid of nuclear localization sequence, and containing another protein or part of a protein that would influence the formation of cell adhesion complexes.

Fusion proteins have been already tested for therapy, primarily anti-cancer therapy. Examples encompass fusion between a drug activator and a tumor specific antibody, an effector of host immune response (e.g. IL2, superantigen) and a tumor specific antibody, an activator of apoptosis (Fas) and the ligand binding domain of Retinoic Acid Receptor, an antibody against a target molecule and the functional domain of an enzyme or a toxin. The present invention represents another level of therapy that would permit the targeted localization of fusion proteins either to the cytoplasm or to the nucleus, by utilizing the multilocalization property of NuMA and its shuttling capacity between the cytoplasm and the nucleus.

The development of such fusion proteins for therapeutic purposes may require the development of systems in order to recognize the cells to be treated (e.g. use of cell specific antibody), like for other type of therapy using fusion proteins. Several systems for intracellular delivery of fusion proteins exist.

The foregoing description of fusion proteins may also be applied to protein complexes, such as protein-protein complexes, protein (NUMA sequence)-small molecule complexes, or protein (NuMA sequence)-nucleic acid complexes.

b) Use of NuMA and proteins behaving similarly to alter biological functions by interacting with docking sites.

The formation of protein multicomplexes plays a key role at all levels of the regulation of cell function. Anchor proteins are supposed to be part of multicomplexes by tethering other proteins to specific target loci. Such tethering results from the interaction between the anchoring protein and other regulatory proteins via docking sites (specific protein sequence). Competition for the same docking site leads to the formation of different multicomplexes of proteins that will have different functions. It has been shown that the introduction of a binding partner for specific docking sites is sufficient to induce specific cellular response by mimicking the interaction found in biological protein complexes. For instance, stimulatory antibodies raised against the docking site of a specific protein have been used to develop therapies for neuroblastoma.

The present invention employs staining techniques based on a two step immunostaining procedure: antibodies specific to NuMA are first introduced to the sample nucleus; then anti-antibodies are introduced in order to bind to and specifically stain the antibody-bound NuMA.

Since we have shown that NuMA plays a key role in maintaining morphogenesis and differentiation of human mammary epithelial cells, it may be possible to regulate differentiation and revert tumor phenotypes by blocking docking sites for proteins that would normally interact with NuMA in tumor cells, or mimicking a protein-protein interaction at the level of docking sites critical for morphogenesis and differentiation.

BRIEF DESCRIPTION OF THE DRAWINGS

The file of this patent contains at least one drawing executed in color. Copies of this patent with color drawings (s) will be provided by the Patent and Trademark Office upon request and payment of the necessary fee.

FIG. 13 (B)(*d–e*). Immulocalization of NuMA in cell matrix preparation using electron microscopy. S1-50 cells that have undergone morphogenesis (acini formation) in 3D cultures have been extracted in situ to prepare cell matrices that contain organized cellular structural components. After epone embedment, thin section were immunostained with anti-NuMA antibodies. NuMA was not only localized in the nucleus (N) (not shown), but also found associated with cytoskeletal structures in the cytoplasm (C). (d): gold beads appearing as black small dots indicate the location of NuMA (mainly seen in the bottom left of the image. (e): Enlargement of a region outlined by a square on image (d) shows four gold beads at the extremity of individual cytoplasmic filaments (arrow). The appearance of image (d) is poor due to loss of resolution after scanning the micrograph. A better visualization of cell structures would be achieved by successfully applying whole mount EM techniques to 3D cultures of cells.

DESCRIPTION OF THE PREFERRED EMBODIMENT

Introduction: Cell Signaling and CMS Proteins

Figure 1:
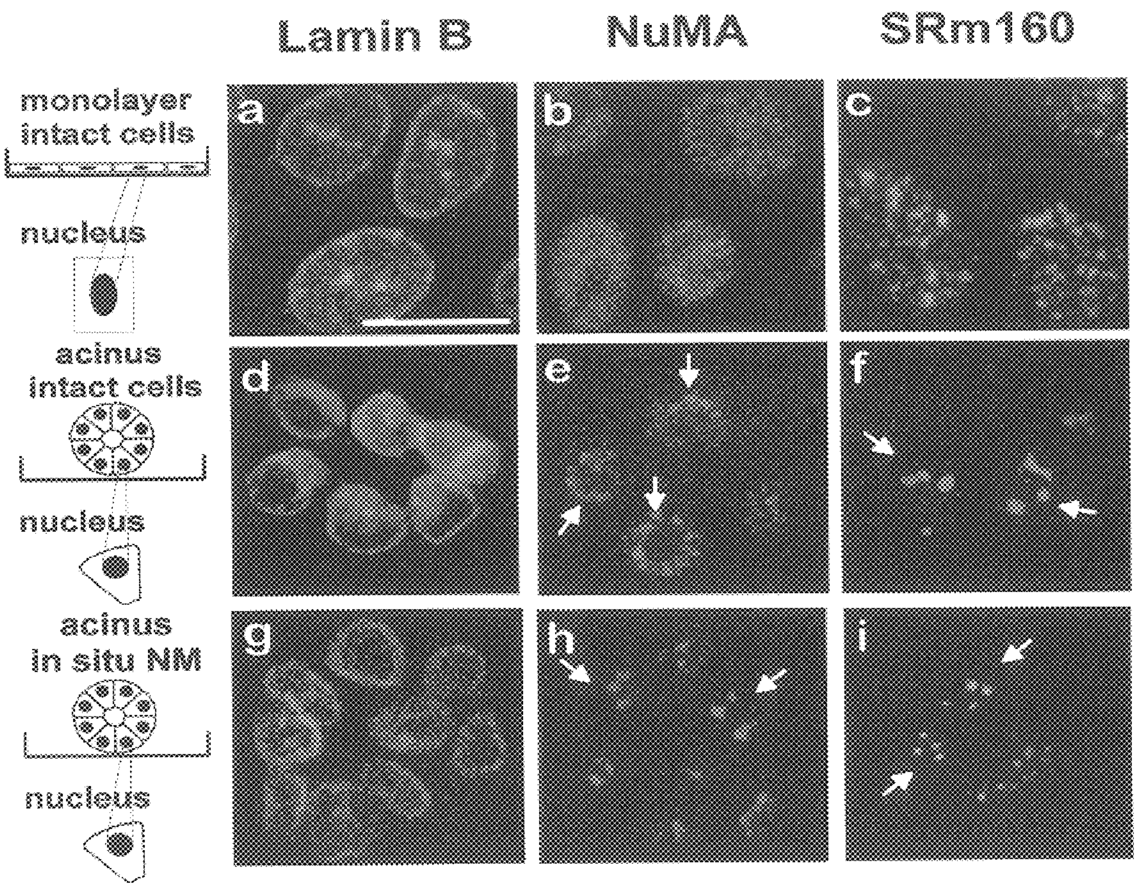
FIG. 1. (*a–i*)NM protein redistribution in HMECs following 3D rBM-induced acinar morphogenesis. Nine cell images: (a, d, g) show cells stained for lamin B, (b, e, h) show cells stained for NuMA, and (c, f, I) show cells stained for splicing factor SRm160(c, f, I).

It is now well established that cell-ECM and cell-cell interactions can regulate gene expression and cell behavior. It is not well understood, however, how information is transduced from the cell membrane to the nucleus. It is known that cell-adhesion-mediated signal transduction is initiated by the supramolecular organization of adhesion molecules and proteins localized on the inner part of the cell membrane, referred to as the membrane skeleton. Communication between spatially separated elements such as the cell membrane and the chromatin requires intracellular mediators, referred to as structural and biochemical signal transducers. Our general understanding is that a signal transducer can receive a signal and transfer the information to the next component of the signaling cascade by altering its molecular state and modifying its binding to other cellular components. Typically, signals initiated at cell adhesion sites, by cell-ECM or cell-cell contacts, are transduced by membrane skeleton proteins, also referred to as junctional plaque proteins. Although these structural signal transducers share common characteristics such as involvement in phosphorylation/dephosphorylation cascades and the capacity to induce cytoskeletal reorganization, they are specific for each type of adhesion complex. Focal adhesions (FAs), a class of cell-ECM adhesion complexes formed by the interaction of various types of integrin heterodimers with specific ECM molecules, contain a large number of connective membrane skeleton (CMS) proteins (e.g. alpha-actinin, talin, tensin, vinculin, Cas, moesin, fimbrin, paxillin and zyxin), that interact with a broad range of kinases and phosphatases, and are implicated in the control of actin and myosin filaments assembly. Similarly, hemidesmosomes are formed by the interaction between the ECM component laminin and alpha6-beta4 integrin, and the recruitment of CMS proteins, plectin and bullous pemphigoid antigen 230, to form the hemidesmosomal plaque. Hemidesmosome formation directs the organization of intermediate filament type proteins and initiates phosphorylation cascades. Cell-cell adhesion complexes (i.e. tight junctions, adherens junctions and desmosomes) have been characterized both microscopically and by their composition. Their localization in a tissue is highly ordered. Tight junctions (zonula occludens) are located at the outermost edge of the intercellular space (i.e. at the apical part of epithelial glandular cell assemblies) and are believed to participate in maintaining cell polarity along with other cell-cell adhesion complexes. Several tight junction-associated CMS proteins have been identified, including ZO-1, ZO-2 and ZO-3, members of the membrane-associated guanylate kinase family (MAGUK), as well as 7H6, cingulin and symplekin. Tight junctions and adherens junctions together form apical junctional complexes. Adherens junction-associated CMS proteins encompass symplekin, plakoglobin, alpha-catenin, beta-catenin, vinculin, and undoubtedly another host of known and unknown proteins, that interact with actin, as is the case also in tight-junctions. Desmosomes constitute a third type of cel-cell junction, where adhesion is mediated through the desmosomal cadherins desmocollin and desmoglein and the CMS proteins desmoplakins and plakoglobin that are connected to intermediate filament type proteins. As with cell-ECM adhesion complexes, cell-cell adhesion complexes interact with various kinases and phosphatases.

Although adhesion complexes are built with different components, they are connected to the same network of cytoskeletal filaments, their integrity depends on tyrosine kinases activity, and they share similar biochemical signal transducers. This indicates that the organization of cell adhesion complexes follows the same linear path from one complex to another, including adhesion molecules linked to complexes of CMS proteins and kinases/phosphatases that regulate the induction of biochemical cascades and the organization of the cytoskeleton, but it does not mean that these structures behave similarly. For instance, treatment with protein phosphatases disrupts FAs and the underlying cytoskeleton, while increased tyrosine phosphorylation induces the redistribution of adherens and tight junction proteins. More specifically, adherens junction disassembly is due to increased phosphorylation mediated through MAP kinase and PI 3-kinase pathways, whereas desmosome disassembly seems regulated by activation of PKC.

Cell adhesion complexes participate in the coordinated regulation of cell division, survival, and differentiation. This coordinated regulation of the cell behavior is mediated by the integration of the linear paths of cell adhesion complexes through interconnection with other signal transduction cascades, and the link between actin and intermediate filament networks. This defines an integrated function for cell adhesion complexes which is ruled by the equilibrium between the different adhesion structures. In addition, alternate construction and deconstruction of cell adhesion complexes has been shown to be critical for developmental programs and cell migration. In this case, modulation of the cellular behavior is due to the switch of dominant signaling pathways which results from equilibrium shifts and temporary delocalization of adhesion proteins and membrane skeleton proteins. However, if there is sustained imbalance, the equilibrium shift may also lead to the stimulation of tumor development.

The CMS proteins, beta-catenin, plakoglobin, plakophilin 2, symplekin, ZO-1, and zyxin have all been observed in the nucleus. Logically, only the CMS proteins free from their interaction with adhesion complexes will translocate into the nucleus. The constitution of a free pool of CMS proteins could result from the expression of these proteins above the level necessary for the formation of adhesion complexes, as it is the case following overexpression of exogenous plakoglobin in transfection experiments. However, CMS proteins are more likely to be observed in the nucleus when the formation of adhesion complexes is impaired, as it has been described in naturally occurring situations. Endogenous beta-catenin has been found in tumor cell nuclei in which cell adhesion complexes were altered. Endogenous symplekin and plakophilin 2 were observed in the nucleus of cells that usually do not form adherens junctions or desmosomes. The presence of endogenous ZO-1 in the nucleus of epithelial cells was inversely correlated with the extent or maturity of tight junctions, and apical polarity in mammary acini. The localization of these CMS proteins in cell adhesion complexes and in the nucleus is not mutually exclusive, since both locations have been simultaneously observed in many cases. This suggests that there may be an equilibrium between membrane skeleton and nuclear localization of the CMS proteins.

The creation of a free pool of CMS proteins via their release from existing cell adhesion complexes or via other mechanisms, is not sufficient to explain how these proteins can enter the nucleus. The study of shuttling proteins has revealed that the mechanisms of nuclear translocation are highly regulated. Translocating CMS proteins may conform to the same mechanisms. It is known that proteins over 40kD actively enter the nucleus by binding to the nucleopore proteins importins via a nuclear localization signal (NLS), and by translocating through the pore via an energy-dependent mechanism. While a putative NLS has been identified in the sequence of both ZO-1 and symplekin proteins, the evidence that these NLS are functional is still lacking. If indeed these are functional, it will be worthwhile to analyze the possible nuclear localization of other NLS bearing CMS proteins (e.g. plectin). The presence of a functional NLS may not be always necessary for the nuclear translocation of CMS proteins. These could 'piggy-back' with other NLS-bearing molecules, as proposed for beta-catenin which travels as a complex with LEF-1. NLS-free CMS proteins could also bind directly to the nuclear pore and translocate into the nucleus, as demonstrated recently for beta-catenin. It will be important to clearly identify those proteins that 'piggy-back' from self translocation of CMS proteins. In the former case, the nuclear translocation is dependent not only on a free pool of CMS proteins but also on the availability of their carrier.

Once CMS proteins are trapped in the nucleus, they may stay there until a signal induces their release from nuclear complexes and initiates their degradation. De novo expression of proteins would re-create the pool of CMS proteins in the cytoplasm. However, since the control of the nuclear translocation of CMS proteins is achieved by their release from interactions with cell membrane and cytoskeletal components, it is possible that similarly their release from interactions with nuclear partners would lead to their return to the cytoplasm. The study of protein shuttling has shown that proteins can slowly diffuse out of the nucleus without any specific signal, while a fast re-entry into the cytoplasm is regulated by pathways distinct from nuclear import mechanisms. The rapid transit of nuclear proteins to the cytoplasm is mediated by nuclear export sequences (NES) via energy-dependent extrusion mechanisms. Previously, only the CMS protein Zyxin has been shown to possess a functional NES, and its traveling into and out of the nucleus has been observed in the course of antibody-injection experiments. However, by analogy with nuclear protein import, it is also possible that certain CMS proteins leave the nucleus by 'piggy-back' riding. Bi-directional transit of zyxin could be regulated by temporarily masking the NES, and/or by the presence of a nuclear retention signal or cytoplasmic retention signal that would be responsible for the binding of the protein to nuclear or cytoplasmic components, as it has been proposed for shuttling proteins. The participation of CMS proteins in the formation of adhesion complexes is an example of cytoplasmic retention.

The preceding discussion illustrates that in a similar manner to CMS proteins, nuclear matrix proteins that shuttle, such as NuMA, may be used to convey information in and out of the nucleus and thereby induce a phenotypic change. The specific embodiment described below may be modified according to the principles outlined above, such as by, using other shuttling proteins, interactions with cell adhesion molecules and nuclear matrix proteins, etc.

NuMA Mediated Changes

Figure 5:
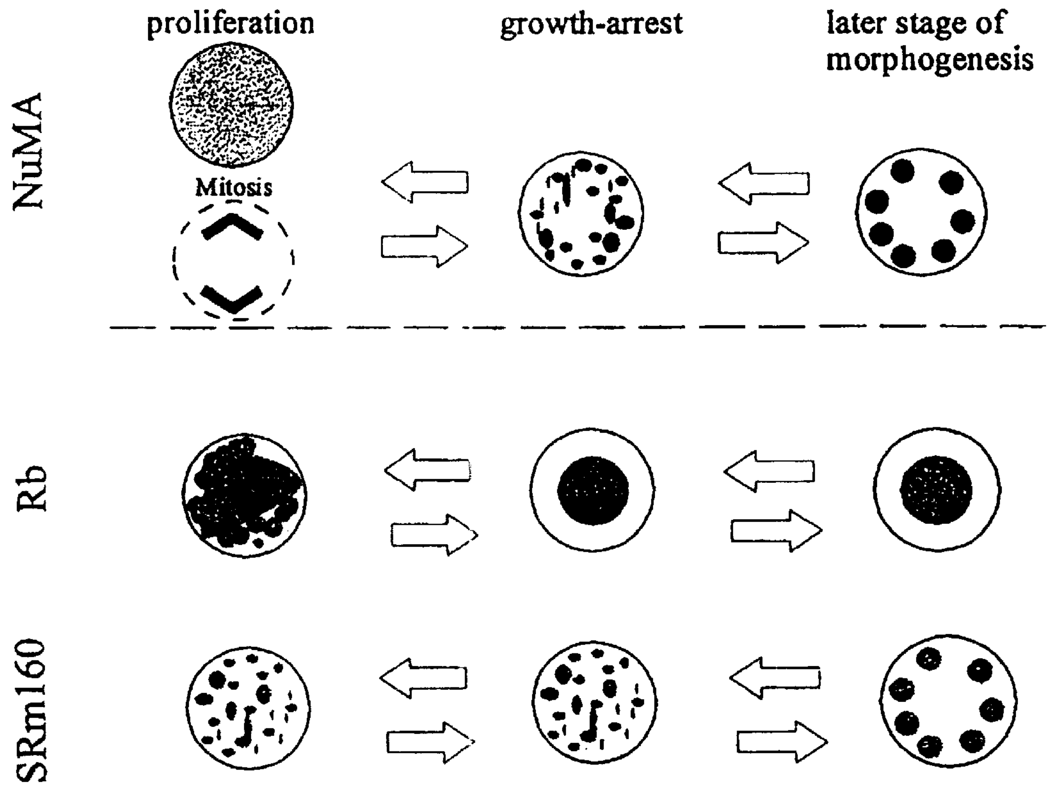
FIG. 5. Schematic Representation of the distribution of Nuclear Matrix Proteins in different stages of mammary acinar morphogenesis.

As shown below in Examples 1–3, by modifying the cellular microenvironment, we have demonstrated that nuclear organization rearranges dramatically in HMECs following growth-arrest and tissue-like acinar morphogenesis (FIG. 5). The use of a 3D rBM culture assay has enabled us to show that alterations of nuclear organization in the acini modify the cellular and tissue phenotype. These results illustrate the interdependence between ECM-cell contacts, nuclear organization and cell and tissue behavior.

Figure 2A:
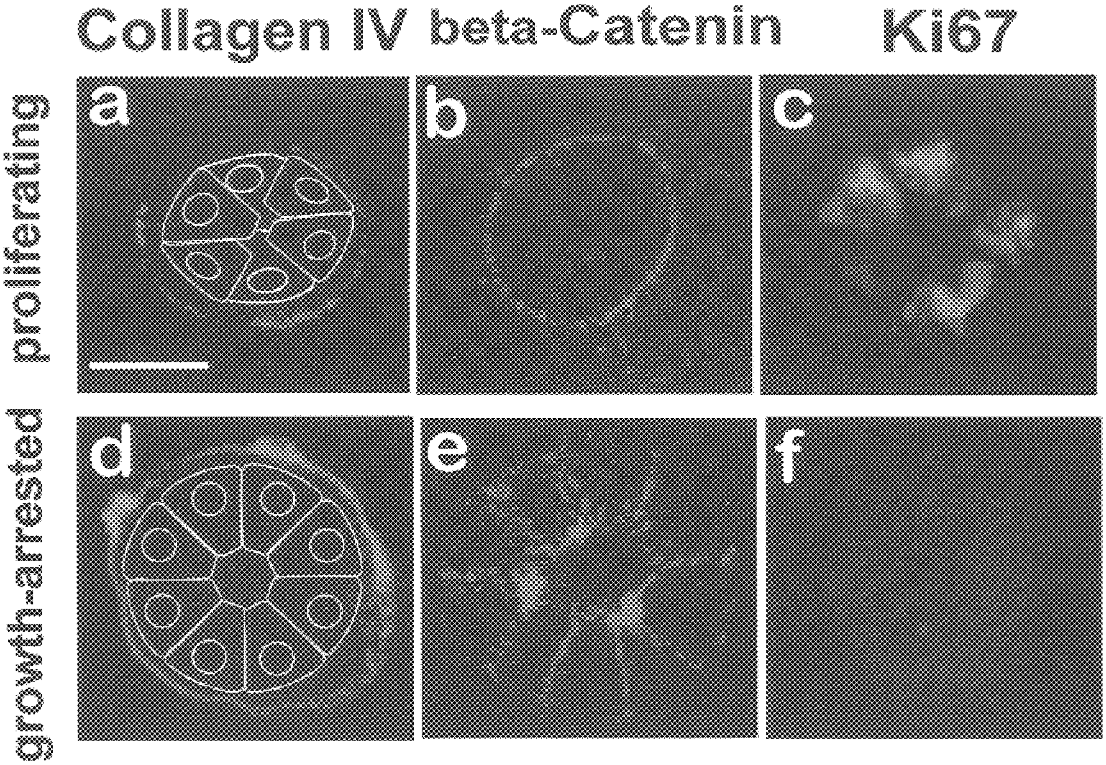
FIG. 2A. (*a–f*)Distribution of structural proteins during rBM-induced acinar morphogenesis. Confocal fluorescence images of stained collagen IV (a, d), β-catenin (b, e), and Ki-67 (c, f) in HMECs embedded within a rBM.
Figure 2B:
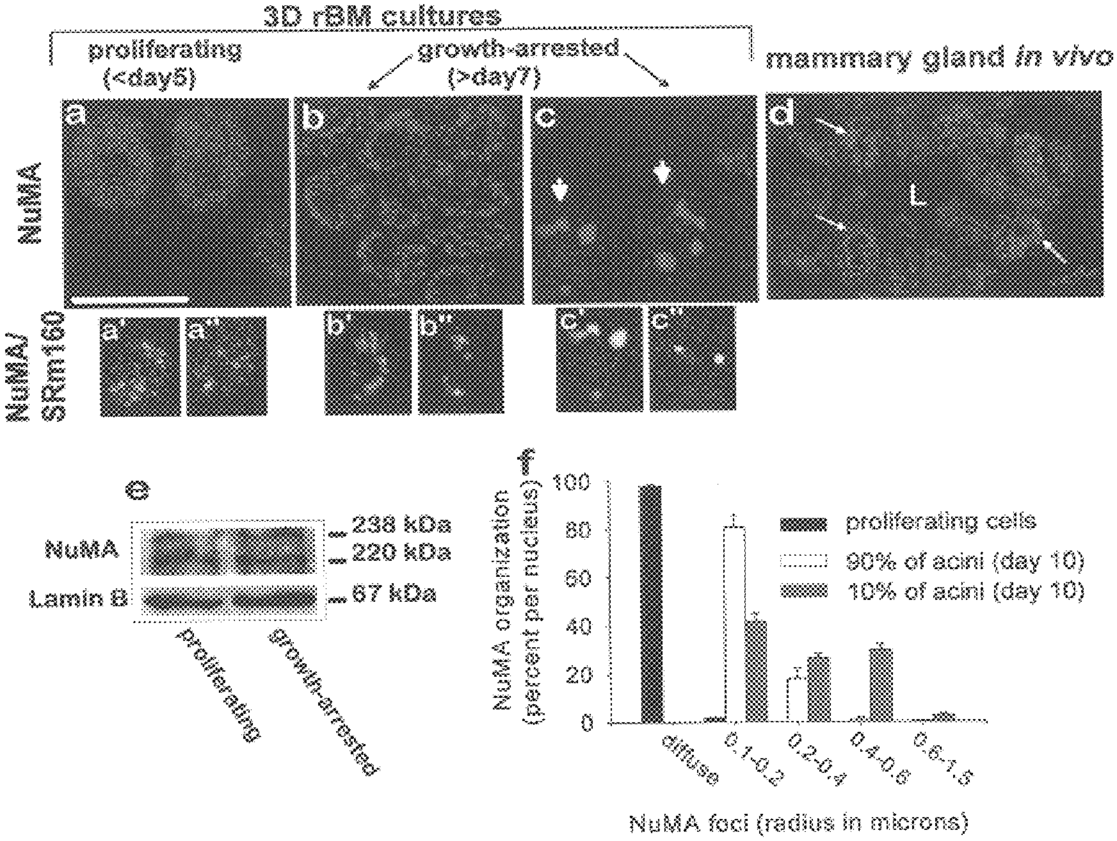
FIG. 2B. (*a,a',a"f*)Spatial analysis of NuMA and Splicing factor SRm160 redistribution during rBM- induced acinar morphogenesis. Confocal fluorescence images of NuMA (Texas red, a–c) and double-labeled NuMA (Texas red) and SRm160(FITC green) (*a',a"–c',c"*) in HMT-3522 cells proliferating (a, a', a"), and undergoing morphogenesis (b, b', b"& c, c', c") in response to a rBM. In the ductal and acinar HMECs of the mammary gland (d), in vivo, NuMA was localized in foci with a size distribution comparable to that observed in most of the HMEC nuclei of differentiating rBM cultures (b). (e) Western blot analysis of NuMA (top) and Lamin B (bottom) showed no difference in protein expression or size between proliferating and growth-arrested HMECs grown within rBMs. Arrows indicate nuclei. (f) is a histogram showing NuMA organization (as percent pre nucleus) vs. NuMA foci (radius in microns).

Thus far documented changes in nuclear organization have been broadly descriptive. By systematically analyzing the distribution of a complement of NM proteins in 2D and 3D cultures of HMECs, we determined that precise nuclear rearrangements occurred with growth-arrest, and following rBM-induced morphogenesis. In 3D rBM cultures, both NuMA and Rb were diffusely distributed in the nucleus of proliferating cells. Following growth-arrest, NuMA was re-localized to discrete foci, while Rb redistributed into a central nuclear mass. These patterns of distribution were different from those observed in growth-arrested cells in monolayer 2D cultures, suggesting that there may be different states of growth-arrest in 2D and 3D rBM cultures. Since NuMA distribution in 3D collagen I cultures was comparable to that observed in growth-arrested 2D cultures, our results suggest that 3D organization of cells per se cannot explain the differences seen between 2D and 3D-rBM cultures, and imply that BM signaling is necessary for the ultimate nuclear organization within the acini. Indeed, the presence of enlarged and peripheral NuMA foci was observed only in mature 3D rBM cultures, and was also found in adult resting mammary gland in vivo, where the acini are surrounded by a continuous endogenous BM. The adult mammary gland undergoes developmental cycles of growth and differentiation; this may account for the heterogeneity of foci size observed in HMECs in vivo, and may further explain the absence of the very large NuMA foci we observed in subpopulations of differentiated 3D rBM-induced acini (FIG. 2B. *c*). Whether the pattern of NuMA distribution indeed corresponds to different levels of differentiation in vivo requires further analysis.

Nuclear organization is modulated by the formation of tissue structure, but it may also regulate cellular and tissue phenotype. The antibody-directed disruption of NuMA foci in the acini induced changes in the distribution pattern of acetylated histone H4, the activation of metalloprotease(s) and the loss of BM integrity. These results, as well as our observation that NuMA progressively coalesces and eventually co-localizes with enlarged splicing factor speckles during acini differentiation, suggests that nuclear proteins of this sort may transfer and/or maintain the molecular information necessary for the development of the acinar phenotype. Interestingly, trichostatin-induced alteration of histone acetylation in acini also led to the disruption of NuMA foci, and was associated with the loss of BM, and the induction of cell proliferation. Although we do not know the molecular mechanisms responsible for phenotypic alterations induced by nuclear reorganization, our experiments clearly demonstrate the existence of reciprocal interactions between nuclear organization, chromatin structure and the acinar phenotype. The BM has been shown previously to be necessary for the formation and maintenance of the functional acinus. We report here that BM-induced acinar formation is associated with the distinct spatial organization of a repertoire of NM proteins, and that conversely, perturbation of nuclear organization alters the BM, and influences the acinar phenotype. These results illustrate the dynamic recip ity between the ECM and the struct organization of the nucleus, and underscore the importance of ECM-NM communication in phenotypic plasticity.

CMS proteins and certain NM proteins like NuMA can be considered as active mediators of the dynamic reciprocity between the microenvironment and the cells. We suggest there is a bi-directional flow of information between the microenvironment and the nucleus, part of which will be dependent on a molecular equilibrium defined by the binding of CMS proteins and NM proteins to their various partners. This concept is well illustrated by the data generated for the CMS protein beta-catenin. Free cytoplasmic beta-catenin, the presence of which depends on its association with other adherens junction molecules and cell membrane receptors, has to override the APC-regulated degradation mechanism before going to the nucleus. The number of free beta-catenin molecules also has to exceed the amount required to form complexes with free ZO-1, that were shown to participate in the formation of tight junctions.

The communication between the cellular microenvironment and the cell nucleus is critical to understanding the essence of cell behavior and tissue development. Signals to be transduced to the cell's interior upon attachment to extracellular matrix (ECM) components or contact with another cell, are mediated by a variety of adhesion molecules. Cell culture systems using a reconstituted basement membrane have enabled a number of laboratories to show that the interaction between adhesion molecules of epithelial cells and basement membrane components induces a differentiation program which leads to the formation of fucctional tissue-like structures. Similarly, the interaction between adhesion molecules of osteoblasts and fibronectin promotes the production of osteopontin, one of the predominant proteins of the bone tissue. ECM-mediated regulation of the expression of a defined repertoire of genes is conveyed, at the molecular level, by a modification of DNA-protein interactions and the activation of ECM-response elements located in the promoters of some of the expressed genes. Cell-cell interaction also induces the expression of specific genes that regulate tissue differentiation and morphogenesis. Moreover, the interplay between the formation and loss of adhesion complexes and the correct balance of different kinds of adhesion molecules is essential for tissue development and maintenance of differentiation, and the alteration of this equilibrium can lead to extreme behavior such as apoptosis and tumor formation.

Computer Algorithm and Analytical Method Used to Evaluate Punctateness

The present invention employs a model-based image analysis algorithm which quantifies the punctateness of NuMA and allows clear distinction not only between growth arrested and proliferating non-malignant cells but also between proliferating non-malignant and malignant cells, cultured as monolayers and in 3D rBM. Cell cultures were imaged in 3D using confocal microscopy, for fluorescently labeled NuMA, Ki-67 and DNA. Nuclear segmentation, based on the DNA staining, allowed image analysis of NuMA staining within individual nuclei.

Ki-67 staining was used to identify cells in the cell cycle. The image analysis algorithm was based on a multi-scale Gaussian blurring method and measured intensity variations within each nucleus. Averaging results over cells in each population resolved significant, yet, sub-visual differences in NuMA punctateness.

Non-malignant growth arrested cells were most punctate, non-malignant proliferating cells produced intermediate values and malignant cells were the least punctate. This ability to discern cell phenotype based on quantifying the spatial distribution of a nuclear protein has broad application in furthering fundamental understanding of biological processes.

MATERIAL AND METHODS

Cell Culture

We used cell lines derived from a reduction mammoplasty: Briand et al.(1 987) In Vitro *Cell. Dev. Biol.* 23, 181–188. S1 cells are non-malignant and form phenotypically normal glandular structures (acini) when cultured in 3D rBM: Petersen OW et al.(1992) *Proc Natl Acad Sci* (USA) 89:9064–9068. T4 cells are malignant cells derived from the S1cells. T4 cells form tumor-like clusters in 3D rBM. HMT-3522 HMECs (S1 passage 50) were propagated in 2D cultures in chemically defined medium and growth-arrest was induced by removing epidermal growth factor (EGF) for 48 hours. 3D cultures were prepared by embedding single cells in rBM (Matrigel™, Collaborative Research) or collagen-I matrix (Cellagen™ AC-5, ICN Biochemicals Incorporated) in four-well chamber slides (Nalge Nunc International). These cultures were grown for 5–10 days. Growth-arrest and morphogenesis were routinely observed by days 7–9. T4 cells were cultured in 2D or 3D in chemically defined medium (Petersen, O. W., R˙ nnov-Jessen L., Howlett, A. R. & Bissell, M. J. (1992) *Proc. Natl. Acad Sci.* (USA) 89, 9064–9068).

Antibodies and Inhibitors

For Western blots and/or immunostaining, we used antibodies against type IV collagen (clone CIV, Dako), β-catenin (clone 14, Transduction Laboratories), SRm160 splicing factor (clone B1C8), lamin B (clone 101-B7, Matritech Inc.), NuMA (clone 204-41, Matritech Inc., and clone B1C11, a gift from Dr. S. Penman), and polyclonal antibodies against Ki-67 (Novocastra Laboratory), acetylated histone H4 (Upstate Biotechnology Incorporated), and p110Rb (Santa Cruz Biotechnology). For bioperturbation assays, we used antibodies against lamins A/C (clone 636, Novocastra Laboratory) and NuMA (clone 22, Transduction Laboratory), in addition to B1C11 and 101-B7. Trichostatin A (Wako Chemicals) was used as an inhibitor of histone deacetylase (40 nM-24 hrs.). Actinomycin D was used as an inhibitor of translocation between the cytoplasm and the nucleus (5 μM, 5 hrs.).

Indirect Immunofluorescence

Cells were perrneabilized in situ (0.5% triton in 100 mM NaCl, 300 mM sucrose, 10 mM PIPES pH 6.8, 5 mM $MgCl_2$, containing 1 mM Pefabloc™, 10 μg/ml leupeptin, 10 μg/ml aprotinin, 10 μg/ml trypsin inhibitor type II, and 250 μM NaF), fixed in 2% paraformaldehyde, and immunostained using standard protocols. Human mammary tissue was snap-frozen in n-hexane and embedded in Tissue-Tek OCT (Miles laboratories); 5μ sections were fixed in methanol and immunostained in accordance with human protocol (KF) 01-216/93 in the laboratory of Dr. O. Petersen.

Image Acquisition, Processing, and Data Analysis

Samples were analyzed using a Bio-Rad MRC 1024 laser scanning confocal microscope attached to a Nikon Diaphot 200 microscope. Fluorescence specificity was ensured by sequential fluorophore excitation. NuMA foci were analyzed using Image Space-3D analysis program (Molecular Probes) and normalized to 3D rBM cluster cell number by highlighting and counting each nucleus using Image Space-measure 2D. The voxel threshold was set at 0.2μ. In a number of experiments NuMA distribution was analyzed using the punctateness algorithm and nuclear segmentation based upon DNA staining. In this case, images were recorded using a Zeiss confocal microscope.

Immunoblot Analysis

Total cell extracts (2% SDS in phosphate buffered saline pH 7.4, containing 1 mM Pefabloc™, 10 μg/ml leupeptin, 10 μg/ml aprotinin, 10 μLg/ml trypsin inhibitor type II, and 250 μM NaF) were prepared in situ for 2D cultures, or on acini isolated from 3D cultures by dispase treatment (5,000 U/ml caseinolytic activity, Collaborative Research). Equal amounts of protein were separated and immunoblotted using standard protocols.

In situ NM Preparation

In situ NM preparation followed the procedure described by: He, D., Nickerson, J.A. & Penman, S. (1990) *J. Cell Biol.* 110, 569–580, except that 0.05 % triton and micrococcal nuclease (5 U/ml; Sigma) were used.

Antibody-mediated Perturbation of Nuclear Organization rBM induced-acini (day 10) were permeabilized for less than two minutes in situ (0.01% digitonin in 25 mM Hepes pH 7.2, 78 mM KHOAc, 3 mM MgHOAc, 1 mM EGTA, 300 mM sucrose, and 1% RIA grade bovine serum albumin), rinsed twice in digitonin-free buffer, and incubated in medium containing dialyzed specific or mock antibodies (15 μg/ml) for 48 hours, after which the cells were incubated with fresh medium for an additional 48 hours. Antibody concentrations and incubation times were determined empirically. Trypan blue dye exclusion tests and apoptosis studies verified the absence of digitonin toxicity.

Electron Microscopy

Three-dimensional cultures were fixed in 2% paraformaldehyde/0.1% glutaraldehyde in Sorensen buffer after in situ nuclear matrix preparation. Cultures were embedded in epone using classical methods and thin sections were immunostained with mouse anti-NuMA antibodies. Gold-labeled secondary antibodies against mouse IgGs were used to reveal NuMA localization.

Fusion Heterokaryon Analysis

Published methods of cell fusion were applied to human mammary epithelial S1-50 or T4-2 cells and mouse 3T3 cells. After a short period of co-culture, cells were treated for 90 seconds with polyethanolglycol, washed in medium and cultured for an extra two, four or six hours, then fixed with 2% paraformaldehyde in cytoskeletal buffer. Immunostaining was performed with a NuMA antibody specific for the human form of the protein (clone 107.7 from Matritech). DNA Dapi staining was used to differentiate human from mouse nuclei, based on the presence of typical large vacuole-like or ring-like structures in the nuclei of mouse cells. Images were analyzed using a Zeiss immunofluorescence microscope.

IMAGE EVALUATION ALGORITHM

The image evaluation algorithm serves as the basis for determining variations in the brightness of NuMA stained regions within a cell nucleus, and in turn the internal nuclear status of a cell. As discussed above, the presence of elevated levels of NuMA at different locations in the nucleus are indicative of the cell phenotype (e.g., proliferating, growth arrested, apoptotic, differentiated, mitotic). By using the method discussed below, fine distinctions in NuMA clumping (called punctateness) may be determined.

In the present method, cells are stained as described earlier, then individual cell nuclei are viewed using a confocal microscope. Serial sections of each cell nucleus are electronically captured. Each image is then divided into a matrix of pixels organized along an x and y axis, and the brightness of each pixel measured. Brightness is measured on a scale of "0" (dark) to "255" (white).

Once the brightness for each pixel is established, a comparison is made to the pixel on its immediate right (y+1 on the y axis). The variation in intensity between each pixel pair is determined using the formula:

$$Isq=(I\ x,\ y-Ix,y+1)^2 \qquad \text{Equation (1)}$$

where Isq is the square of intensity difference, and x,y is the pixel location on the x and y axis, respectively.

Then Isq is summed for all values of x and y in the image (including all serial sections of a nucleus). This gives the Total Intensity square (tIsq).

The VARIANCE unit is the square root of tIsq $$Var=\sqrt{tIsq} \qquad \text{Equation (2)}$$

The VARIANCE number is the total of Intensity units for all serial sections. This is the adjusted VARIANCE unit for a nucleus.

The process is repeated; however, this time the variance number is determined by comparing the differences between adjacent pixels after the image is blurred using a "Gaussien smoothing algorithm". Commonly available algorithms of this type may be used. The smoothing algorithm removes rapid variations that occur between adjacent pixels.

The smoothing algorithm is used to determine a unit of variation for each pair of adjacent pixels. Again the variance number for the blurred image is calculated using equations (1) and (2). Blurring is measured in incremental steps until the contrast in pixel intensity disappears. The variance number of each blurring step is divided by the variance number of the "non-blurred" image. This normalizes for differences in nuclear volume, background and staining intensity. The resulting numbers are plotted on a standard x (value of the resulting numbers) and y (blurring step) axis. This measurement process is useful in distinguishing significant differences in the distribution of NuMA protein within the nucleus.

The presesntly preferred smoothing program uses incremental "blur factors" that re[resent the width of the Gaussian distribution about a data point. The larger the spread of data, the larger the blur. A "blur factor of 4" represents a smoothing width (or standard deviation if you like) of 0.353 pixels in the image.

Figure 9:
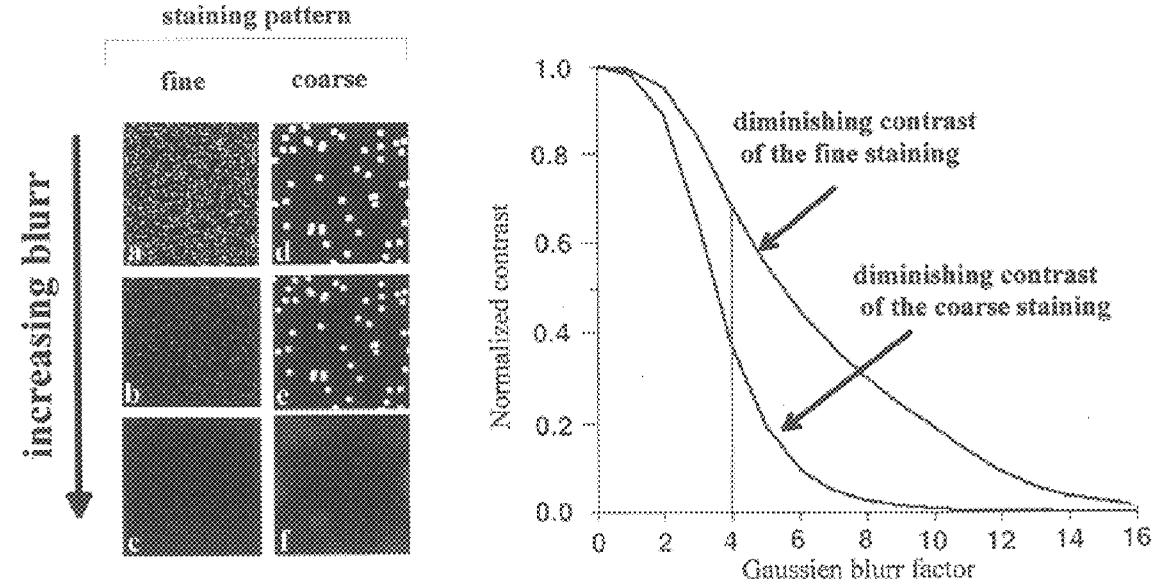
FIG. 9. Mathematical modeling of the measurement of punctateness.
Figure 10:
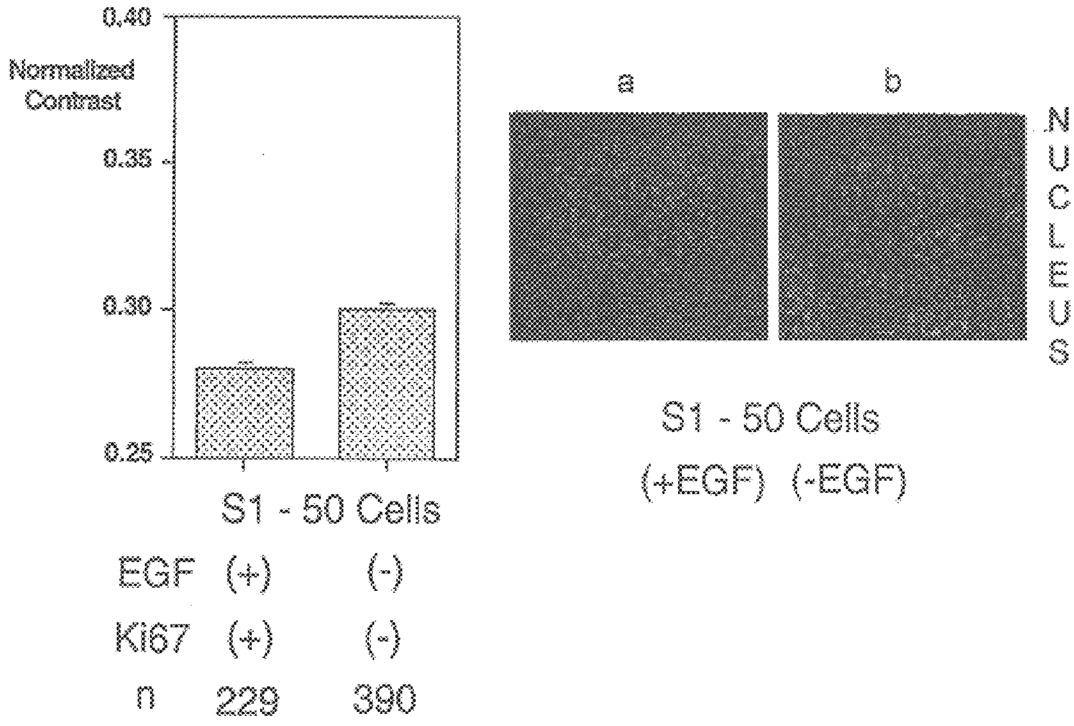
FIG. 10. Measurement of NuMA punctateness in proliferating and growth-arrested S-50 cells cultured as monolayers (2D). As it is shown in Example 2, NuMA distribution looks more aggregated when S1-50 cells are growth-arrested compared to proliferation. As an indication of the usefulness of the algorithm to measure subtle differences in NuMA distribution, we recorded and tested images of NuMA staining in proliferating (+EGF) (a) and growth-arrested (−EGF) (b) cells. Topro-3 (Molecular Probes, Inc.) was used as a counterstaining for DNA which permitted the nuclear segmentation and the reconstruction of the entire nuclear volume. Calculations clearly indicated that NuMA staining is significantly more punctate (or less diffuse) in the nucleus of growth-arrested cells compared to proliferating cells, as shown by the higher level of contrast for NuMA staining in growth-arrested cells, hence corroborating the difference in NuMA distribution directly seen with the microscope. The histogram shows the results calculated for the fourth blurring step. Ki67 indicates that cells are in the cell cycle (+) or out of the cell cycle (−). n is the number of nuclei analyzed.
Figure 14:
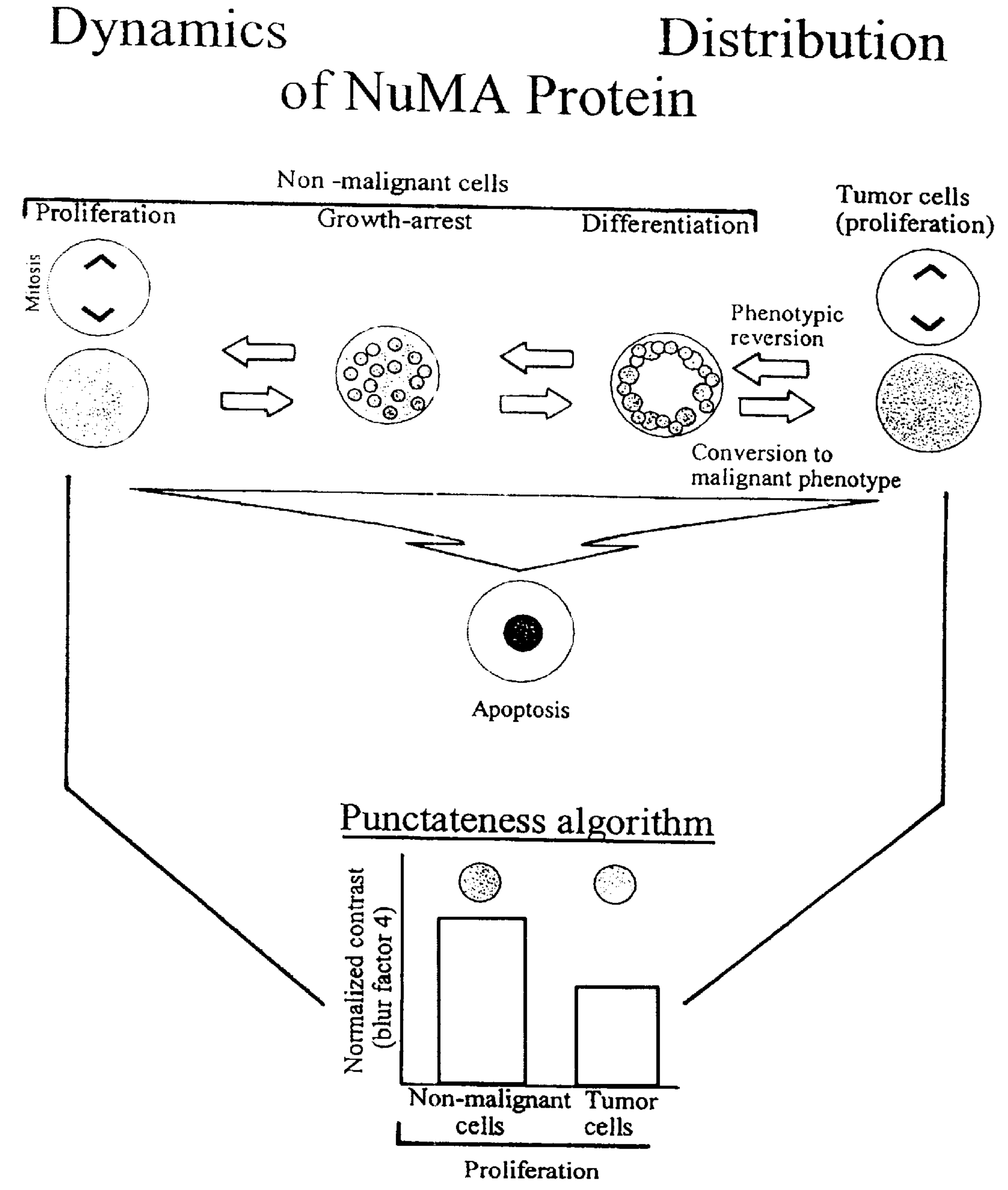
FIG. 14. Schematic representation of the distribution of NuMA in various cell phenotypes, including proliferation, mitosis, growth-arrest, differentiation, and apoptosis. The use of a punctateness algorithm is also indicated as a tool to discriminate NuMA distribution between proliferating non-malignant cells and proliferating malignant cells.

This evaluation process is shown and discussed in FIG. 9. FIGS. 5 and 14 illustrate generally the distribution of NM proteins and the distribution of NuMA protein associated with the present invention.

Referring now to FIG. 5, there is illustrated a schematic representation of the distribution of Nuclear Matrix Proteins in different stages of mammary acinar morphogenesis. Onlu NuMA shows three different patterns of punctateness (distribution). The Rb and SRm160 patterns illustrate the patterns shown in different nucleii with regard to known markers for cell differentiation.

EXAMPLES

Example 1

Internal Nuclear Organization Is Remodeled When HMECS Are Cultured Within 3D rBM.

HMT-3522 HMECs, like primary HMECs, undergo morphogenesis to form tissue-like acini when cultured in 3D rBM. Neither cell type undergoes acinar differentiation when cultured as 2D monolayers.

Referring now to FIG. 1, confocal fluorescence irnages (0.2$\mu$ optical sections) of lamin B, NuMA and splicing factor SRml60 in cells grown as monolayers (2D),( a–c) and within rBMs (3D), (d–i) are shown. NuMA was diffusely distributed in the nuclei of cells grown as monolayers (b), but reorganized into large nuclear foci in cells induced to undergo morphogenesis (acini formation) in response to a rBM (e). SRm160 was distributed as multiple nuclear speckles in cells cultured as monolayer (c), whereas it was concentrated into fewer and larger speckles in the acini (f). Lamin B in contrast, consistently localized to the nuclear periphery and within intra nuclear patches (a & d). The distribution of lamin B (g), NuMA (h) and SRm160 (i) after in situ NM preparation of cells cultured in 3D rBM was similar to that observed in intact cells (d–f). Scale bar 10$\mu$. Arrows indicate nuclei found within the plane of the section.

In proliferating 2D cultures, NuMA was diffusely distributed in the nucleus (FIG. 1*b*) except when localized to the spindle poles in mitotic cells, while splicing factor SRm160 was distributed into numerous speckles of heterogeneous sizes (FIG. 1*c*). In rBM-induced acini, NuMA was distributed into an average of eight nuclear foci (ranging from 1 to 1.6$\mu$ in diameter), surrounded by diffusely localized NuMA protein (FIG. 1*e*), and SRm160 was distributed into a few large speckles (mean of seven) (FIG. 1*f*). In contrast, lamin B maintained a peripheral ring-like distribution around the nucleus, with some internal localization, regardless of culture conditions (FIGS. 1*a* and *d*). The distribution pattern of these proteins was conserved in NM preparations in situ, where chromatin was removed before immunolocalization (staining is shown for 3D rBM cultures only, FIG. 1*g–i*).

We next examined NuMA and SRm160 distribution at different stages of 3D rBM-induced morphogenesis . Referring now to FIG. 2A, confocal fluorescence images (0.2$\mu$optical sections) of collagen IV, β-catenin and Ki-67 antigen in HMECs embedded within a rBM for 3–4 days (proliferating cells, a–c), and for 7–10 days (growth-arrested acini, d–f). Coincident with growth-arrest and acinar morphogenesis, HMECs deposited an organized endogenous collagen IV-rich BM (compare a with d), while β-catenin re-localized from the cytosol and basal plasma membrane to sites of cell-cell adhesion (compare b with e). Acinar morphogenesis was associated with cell-cycle exit, as indicated by the loss of Ki-67 staining (compare c with f). Scale bar 10$\mu$.

After embedment in rBM, cells proliferated to form small clusters but had not organized adherens junctions or assembled an endogenous BM, shown by lack of cell-cell β-catenin and discontinuous collagen IV staining (days 3–5; FIG. 2A. *a–c*). Following growth-arrest, cells assembled a continuous endogenous BM, and formed polarized acinus-like structures with cell-cell β-catenin (days 6–10; FIG. 2A. *d–f*).

Referring now to FIG. 2B, there is shown confocal fluorescence images (0.2$\mu$ optical sections) of NuMA (Texas red, a–c) and double-labeled NuMA (Texas red) and SRm160 (FITC green) (a',a"–c',c") in HMT-3522 cells proliferating (a, a', a"), and undergoing morphogenesis (b, b', b"& c, c', c") in response to a rBM. In proliferating cells NuMA was diffusely distributed (a) and did not co-localize with SRm160 (a'& a"). Following growth-arrest NuMA coalesced into foci of increasing size (0.2–2 $\mu$, f) in association with the establishment of mature tissue-like structures (acini) (b–9 nuclei shown, & c). Only the larger NuMA foci observed in late morphogenesis fully co-localized with SRm160 (b', b"–c', c"). (d) In the ductal and acinar HMECs of the mammary gland, in vivo, NuMA was localized in foci with a size distribution comparable to that observed in most of the HMEC nuclei of differentiating rBM cultures (b). (e) Western blot analysis of NuMA (top) and Lamin B (bottom) showed no difference in protein expression or size between proliferating and growth-arrested HMECs grown within rBMs. Scale bar 10$\mu$. Arrows indicate nuclei.

NuMA was uniformly distributed in the nuclei of proliferating cells (FIG. 2B. *a*), but became concentrated into distinct foci of differing sizes following growth-arrest (day 7; FIG. 2B. *b*), and into larger and fewer foci upon completion of morphogenesis (day 10, FIG. 2B. *c*). NuMA and the splicing factor SRm160 were not co-localized in proliferating cells (FIG. 2B. *a*' and *a*"), but NuMA foci and SRm160 speckles were close together following growth-arrest (FIG. 2B. *b*' and *b*"), and were completely co-localized in large assemblies after the completion of morphogenesis (FIG. 2B. *c*' and *c*"). These spatial changes in NuMA arrangement occurred without significant modifications in NuMA expression or size, as determined by western blot analysis (FIG. 2B. *e*). Since the existence of NuMA in differentiated tissue has been questioned, we studied NuMA in normal resting human mammary gland. Intense staining was observed in the epithelial cells of acini and ducts where NuMA was distributed in foci of different sizes, resembling the acinar stage recapitulated in 3D rBM cultures (FIG. 2B. *d*). These experiments demonstrate that specific NM proteins undergo spatial rearrangement during rBM-induced acinar morphogenesis.

Example 2

Growth-Arrest Is Associated With Changes In NuMA And Rb Distribution

ECM-directed growth-arrest is an early and critical step in mammary epithelial cell morphogenesis. To distinguish between the effect of ECM-directed growth-arrest and changes due to tissue structure and polarity, the localization of NuMA and SRm160 was compared between growth-arrested and proliferating cells cultured as 2D monolayers. Less than five percent of the cells remained in the cell cycle following growth-arrest induced by EGF removal, as indicated by the absence of detectable Ki-67 immunostaining (not shown). NuMA was uniformly distributed in the nuclei of proliferating cells, but coalesced into denser areas upon growth-arrest.

Figure 3:
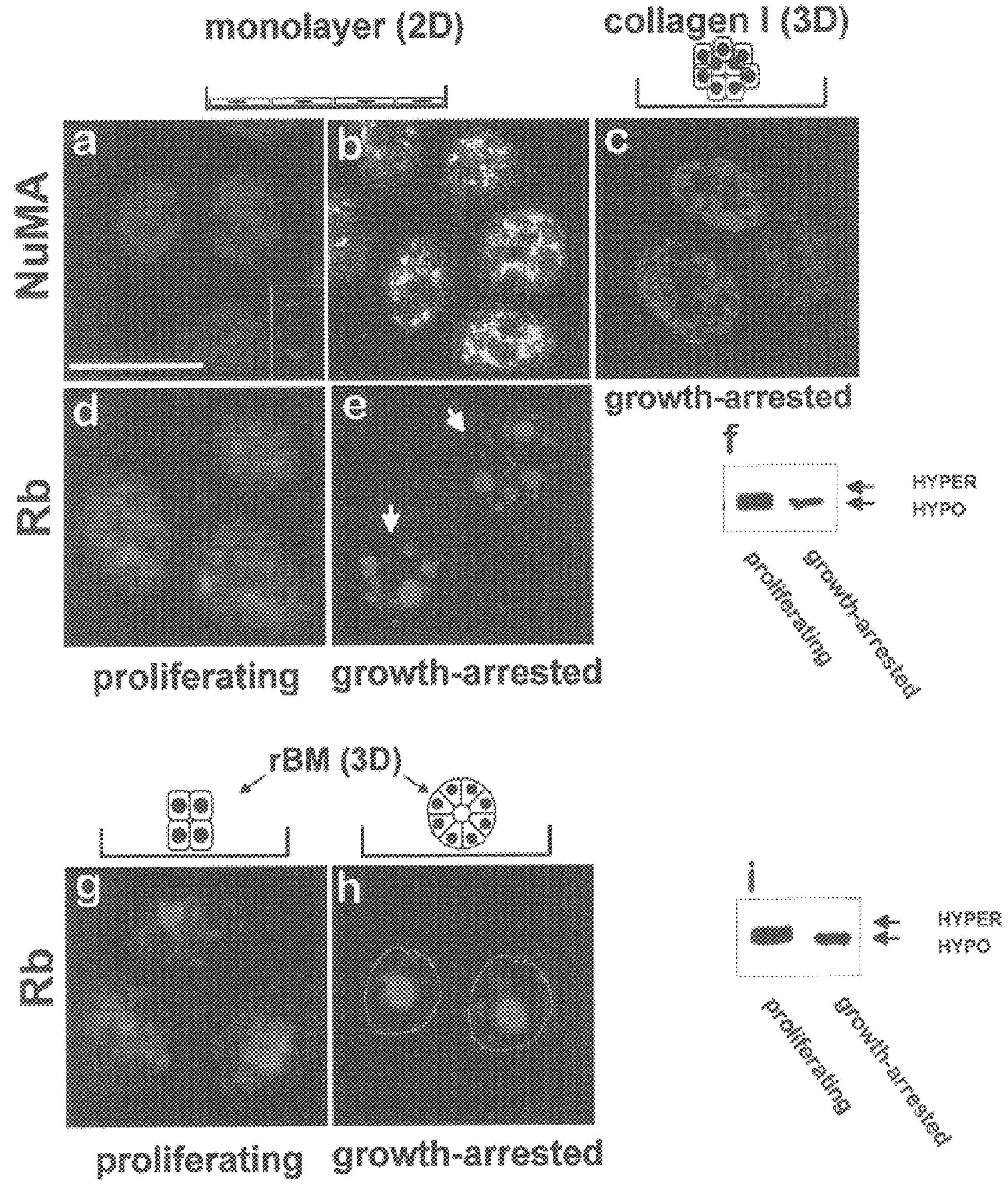
FIG. 3. (*a–i*) Effect of growth status on the distribution of NM proteins. Confoal fluorescence images (0.2μoptical sections) of NuMA (Texas red, a–c) and Rb (FITC green, d, e, g, h) in cells proliferating as 2D monolayers (a & d) and within 3D rBMs (g), and cells growth-arrested in monolayer (b & e) and within collagen-I (c) or a rBM (h). NuMA was diffusely distributed in the nucleus of proliferating HMECs grown as monolayers (a) and reorganized into random aggregates upon growth-arrest induced by EGF removal (b; the settings for image recording were the same as for image a; aggregates appear in white due to saturation of the signal). NuMA was distributed in random aggregates or in small foci in growth-arrested and BM-free cell colonies obtained after 10 days of culture within collagen-I (c). Rb was diffusely distributed in the nucleus of proliferating cells grown either in monolayer (d) or in 3D rBM (g), however, upon growth-arrest the protein redistributed into several foci in the monolayer propagated cells (e) but coalesced into a central, single nuclear focus in the rBM-induced acini (h; the dotted line indicates outer nuclear limit). Western blot analysis of Rb in proliferating and growth-arrested cells grown as monolayers (f) or within a 3D rBM (i) shows that the hyperphosphorylated isoform was only present in proliferating cells. Scale bar represents 10μ. Arrows indicate nuclei.

Referring now to FIG. 3, there is shown confocal fluorescence images (0.2$\mu$ optical sections) of NuMA (Texas red, a–c) and Rb (FITC green, d, e, g, h) in cells proliferating as 2D monolayers (a & d) and within 3D rBMs (g), and cells growth-arrested in monolayer (b & e) and within collagen-I (c) or a rBM (h). NuMA was diffusely distributed in the nucleus of proliferating HMECs grown as monolayers (a) and reorganized into random aggregates upon growth-arrest induced by EGF removal (b; the settings for image recording were the same as for image a; aggregates appear in white due to saturation of the signal). NuMA was distributed in random aggregates or in small foci in growth-arrested and BM-free cell colonies obtained after 10 days of culture within collagen-I (c). Rb was diffusely distributed in the nucleus of proliferating cells grown either in monolayer (d) or in 3D rBM (g), however, upon growth-arrest the protein redistributed into several foci in the monolayer propagated cells (e) but coalesced into a central, single nuclear focus in the rBM-induced acini (h; the dotted line indicates outer nuclear limit). Western blot analysis of Rb in proliferating and growth-arrested cells grown as monolayers (f) or within a 3D rBM (i) shows that the hyperphosphorylated isoform was only present in proliferating cells. Scale bar represents 10μ. Arrows indicate nuclei.

The irregular geometric quality of these dense areas was distinct from the circular foci pattern observed in growth-arrested 3D rBM-grown cells. In contrast, no significant change in the multi speckled distribution of SRm160 was detected under these conditions (not shown). The relationship between nuclear organization and growth status was further investigated by examining the distribution of the cell cycle regulator Rb. Rb redistributed from a diffuse nuclear pattern in proliferating HMECs, into a few large foci in growth-arrested cells (FIGS. 3*d–e*). Strikingly, the distribution of Rb in the growth-arrested 2D cultures was distinct from that observed in the growth-arrested 3D cultures (compare FIGS. 3*e* to 3*h*), which may reflect differences in the state of growth arrest between 2D monolayer and 3D rBM cultures. The mono-focal pattern of Rb observed in 3D culture was coincident with growth-arrest. Western blot analysis showed that hypophosphorylated Rb was associated with the NM in 3D cultures (not shown), as was previously reported for 2D cultures. Moreover, the diffuse distribution observed in proliferating cells was associated with the hyperphosphorylated form of the protein (FIGS. 3*f* and 3*i*).

Since growth-arrest in 3D rBM precedes the final stages of acinar morphogenesis, we examined the relationship between the large NuMA foci and the formation of a polarized endogenous BM. HMECs cultured in a 3D collagen-I matrix form growth-arrested organized colonies, but do not assemble a polarized, endogenous BM. Therefore, we compared NuMA distribution in cells grown in rBM to those grown in type I collagen. After 12 days in collagen I, NuMA was distributed as small foci or irregular dense aggregates (FIG. 3*c*), similar to the pattern observed in growth-arrested cells in 2D cultures. Thus, NuMA redistribution into dense areas and small foci is induced by growth-arrest, but the coalescence of the foci into larger and distinct structures requires the presence of a polarized BM.

Example 3

Figure 4:
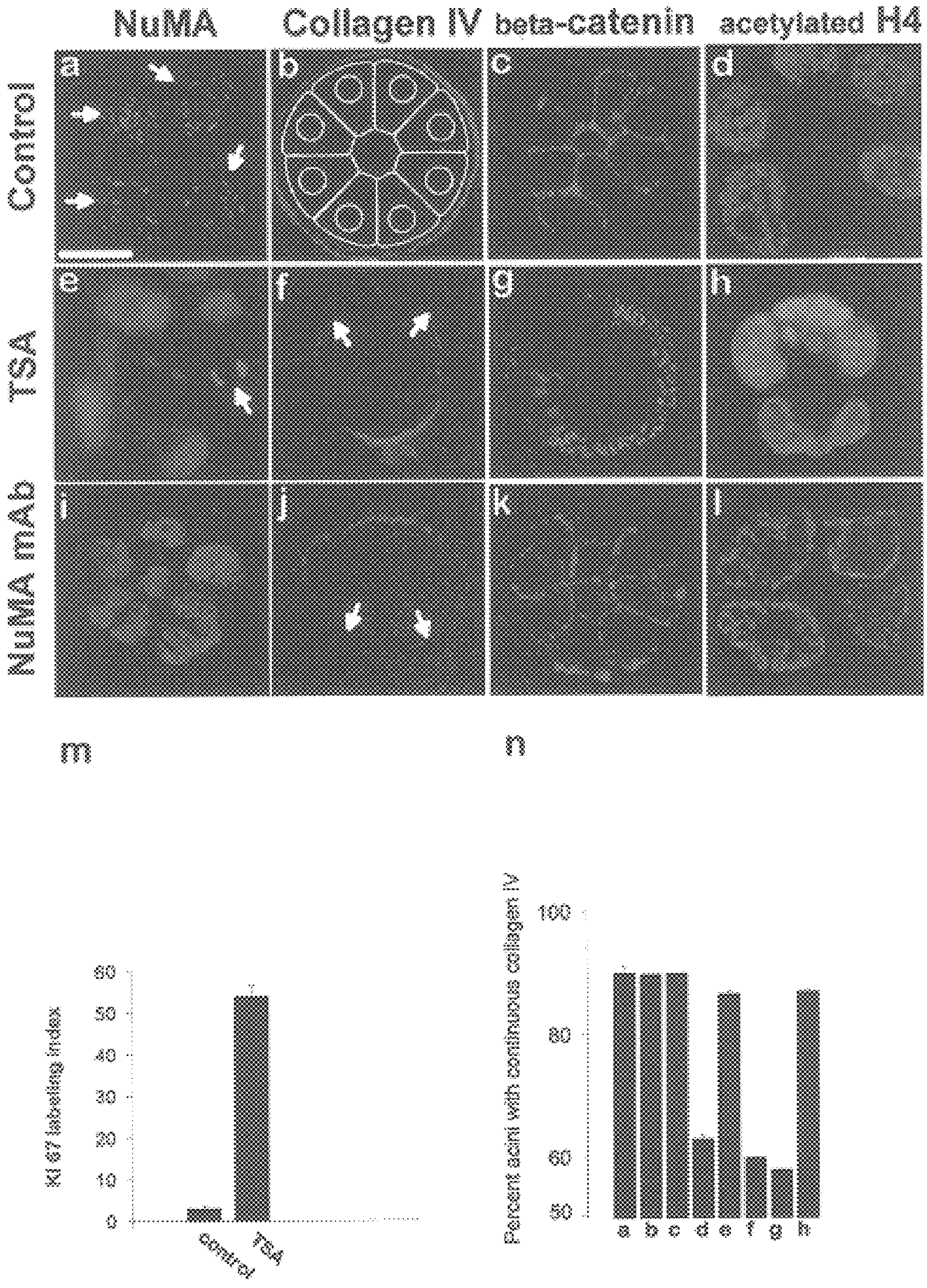
FIG. 4. (*a–n*) Cross-modulation between chromatin structure, NM organization and the acinar phenotype. Confocal fluorescence images (0.2μ optical sections) of NuMA (a,e,i,) collagen IV (b,f,j,) β-catenin (c,g,k) and acetylated histone H4(d, h,l) in control, trchostatin A (TSA)-treated and NuMA monoclonal antibody (mAb)-incubated acini (day10 of 3D rBM culture. (a–d) Nuclear organization and acinar phenotype in controls: acini exhibit NuMA foci (a), an organized endogenous collagen IV-rich BM (b), cell-cell localized β-catenin (c) and disersed acetylated H4 histone (d). (e–h) Effects of TSA on nuclear architecture and acinar phenotype: following 24 hours of TSA treatment (40 nM), more then 55 percent of the cells entered the cell cycle, as indicated by an increase in Ki-67 labeling index (m) and the appearence of mitotic cells (e;arrow). NuMA was uniformly distributed in the nuclei (e), collagen IV disappeared (f), β-catenin was released from the cell-cell interface (g), and the pattern of histone H4 acetylation was altered (h). (i–l) Effects of mAb-induced NuMA foci disruption on nuclear organization and acinar phenotype: introduction of a NuMA mAb into the nuclei of the acini, using reversible digitonin permeabilization, led to the disruption of NuMA foci (i), degradation of collagen IV-rich BM (j; arrows), and the nuclear marginalization of acetylated H4 histone (l). There was no consistent alterations observed for β-catenin other then increased basal labeling (k). These effects were not observed using mock IgG's or mAb to lamins A/C or B. (n) BM degradation following mAb-induced NuMA disruption in acini: analysis of the percentage of acini with intact collagen IV-rich Bms in relation to (a) control/digitonin-permeabilized (DP) acini, (b) mock-IgG mAb-treated/DP acini, (c) NuMA mAb-treated/non-permeabilized acini, (d) NuMA mAb-treated/DP acini, (e) NuMA mAb-treated/DP acini+the metaloproteinase inhibitor GM 6001, (f) NuMA mAb-treated DP acini+the inactive metaloproteinase inhibitor GM1210, (g) NuMA mAb-treated/DP acini+the uPa inhibitor, aprotinin, and (h) Lamian B mAb-treated/DP acini. More then 35 percent of acini degraded their endogenous BMs in response to disruption of MuMA (d). The BM loss could be rescued by treatment with the metalloproteinase inhibitor GM6001 (e), but not its inactive analougue (f) or a uPA protease inhibitor (g). Scale bar 10$\mu$.

Cross-Modulation Between NuMA Distribution, Chromatin Structure, And The Acinar Phenotype The degree of histone acetylation has been shown to regulate chromatin structure and gene expression. Histone acetylation was altered in the acini using the histone deacetylase inhibitor trichostatin A. After two hours of treatment NuMA foci began to disperse, and several cells entered the cell cycle, as measured by an increase in the Ki-67 labeling index. Referring now to FIG. 4, there is shown confocal fluorescence images (0.2μ optical sections) of NuMA (a, e, i), collagen IV (b, f, j), β-catenin (c, g k) and acetylated histone H4 (d, h, l) in control, trichostatin A (TSA)-treated and NuMA monoclonal antibody (mAb)-incubated acini (day 10 of 3D rBM culture). (a–d) Nuclear organization and acinar phenotype in controls: acini exhibit NuMA foci (a), an organized endogenous collagen IV-rich BM (b), cell-cell localized β-catenin (c) and dispersed acetylated H4 histone(d). (e–h) Effects of TSA on nuclear architecture and acinar phenotype: following 24 hours of TSA treatment (4nM), more than 55 percent of the cells entered the cell cycle, as indicated by an increase in Ki-67 labeling index (m) and the appearance of mitotic cells (e; arrow). NuMA was uniformly distributed in the nuclei (e), collagen IV disappeared (f), β-catenin was released from the cell-cell interface (g), and the pattern of histone H4 acetylation was altered (h). (i–l) Effects of mab-induced NuMA foci disruption on nuclear organization and acinar phenotype: introduction of a NuMA mAb into the nuclei of the acini, using reversible digitonin permeabilization, led to the disruption of NuMA foci (i), degradation of the collagen IV-rich BM 0; arrows), and the nuclear marginalization of acetylated H4 histone (1). There was no consistent alterations observed for β-catenin other than increased basal labeling (k). These effects were not observed using mock IgG's or mAbs to lamins A/C or B. (n) BM degradation following mAb-induced NuMA disruption in acini: analysis of the percentage of acini with intact collagen IV-rich BMs in relation to (a) control/digitonin-permeabilized (DP) acini, (b) mock-IgG mAb-treated/DP acini, (c) NuMA mAb-treated/non-permeabilized acini, (d) NuMA mAb-treated/DP acini, (e) NuMA mAb-treated/DP acini+the metaloproteinase inhibitor GM6001, (f) NuMA mAb-treated/DP acini+the inactive metaloproteinase inhibitor GM1210, (g) NuMA mAb-treated/DP acini+the uPA inhibitor, aprotinin, and (h) Lamin B mAb-treated/DP acini. More than 35 percent of acini degraded their endogenous BMs in response to disruption of NuMA (d). The BM loss could be rescued by treatment with the metalloproteinase inhibitor GM6001 (e), but not its inactive analogue (f) or a uPA protease inhibitor (g). Scale bar 10μ.

After 24 hours of treatment, NuMA was diffusely distributed in all nuclei (FIG. 4*e* compared to 4*a*); the acinar phenotype was altered as shown by loss of the endogenous BM (FIG. 4*f* compared to 4*b*), cytoplasmic and basal acini surface redistribution of β-catenin (FIG. 4*g* compared to 4*c*), and the presence of mitotic cells, shown by mitotic spindle pole staining of NuMA (FIG. 4*e*, arrowhead). In contrast, trichostatin A did not alter the cell phenotype, or the distribution of NuMA, in proliferating cells in early 3D rBM cultures.

Since NuMA is essential for nuclear assembly following mitosis and participates in the loss of nuclear integrity during apoptosis, we asked whether disruption of NuMA foci in the acini could globally influence nuclear organization and affect the acinar phenotype. Rapid and reversible digitonin permeabilization was used to load cells with either anti-NuMA mabs, or with an $IgG_1$ mock mAb. The NuMA mAb B1C11, but not an N-terminal-specific mAb (clone 22), disrupted NuMA organization, causing the protein to become diffusely redistributed within the nucleus, as revealed using secondary antibody (FIG. 4*i*). Chromatin structure was altered, as shown by the rearrangement of acetylated histone H4 distribution (compare FIGS. 4L and 4*d*). More dramatically, disrupting NuMA organization altered the acinar phenotype, shown by loss of the endogenously organized BM component, collagen IV (FIG. 4*j*), which could be prevented by treatment with GM6001, a potent metalloprotease inhibitor (FIG. 4*n*). This indicates that NuMA redistribution led to an induction and/or activation of a metalloprotease. Similar treatment of the acini with mAbs against lamins A/C or lamin B did not induce any change in histone H4 acetylation, BM integrity or lamin distribution, although these antibodies did reach their nuclear targets, shown by secondary mAb staining (FIG. 4*n* and not shown).

Example 4

Figure 6:
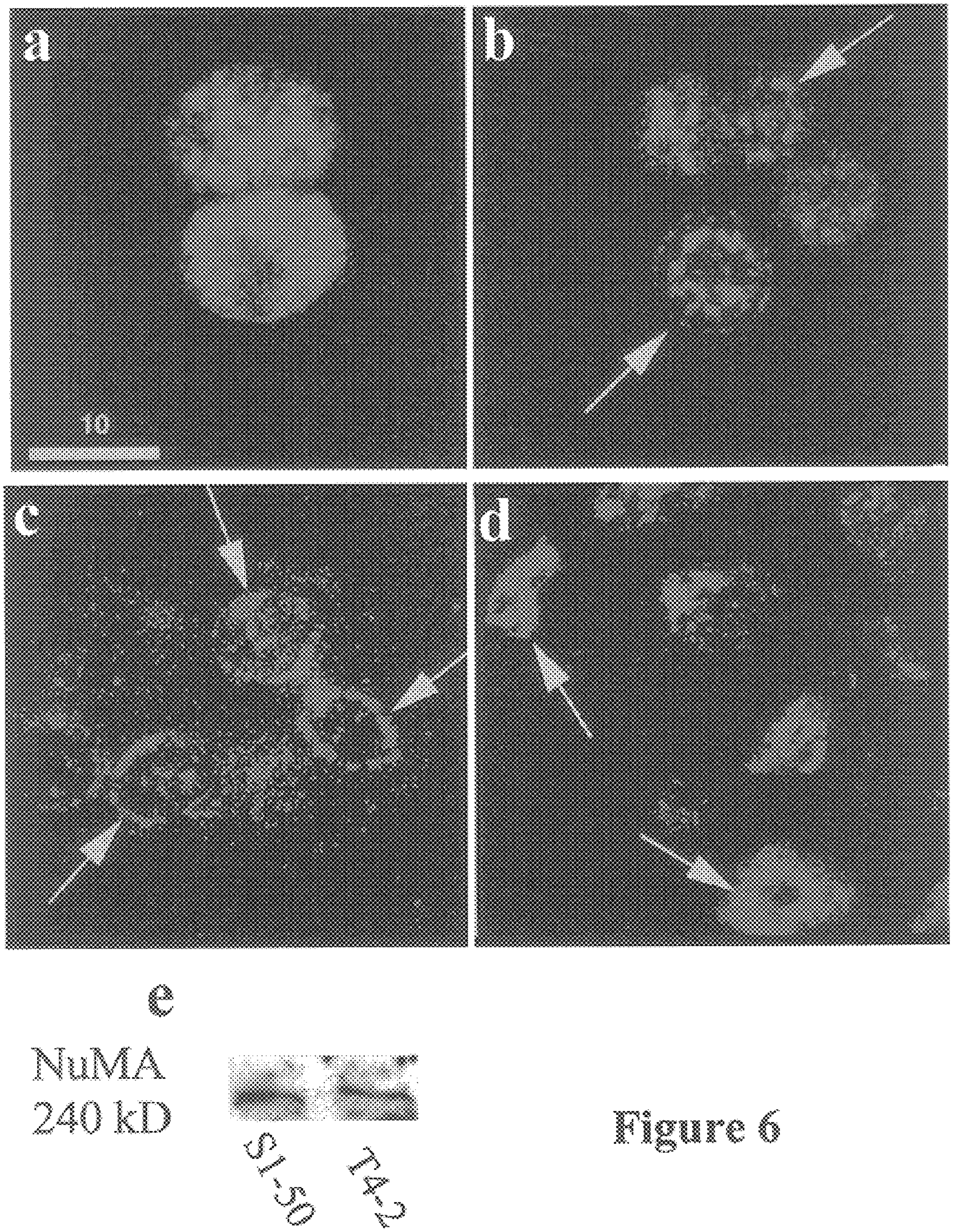
FIG. 6. (*a–e*) NuMA distribution in tumor T4-2 cells and non-malignant S1-50 cells grown in 3D-rBM culture Day10 of 3D culture T4-2 cells form disorganized clusters in which nuclear NuMA is diffusely distributed (d), whereas NuMA is concentrated into enlarged foci at the periphery of the nuclei of non-malignant cells that have undergone acinar morphogenesis (b). Moreover, it is possible to follow the stepwise reorganization of NuMA in non-malignant cells up to day 10: in early culture (day 3), cells are proliferating and display a diffuse distribution pattern for NuMA (a), as the cells arrest growth (day 5–6) they show a patchier distribution for NuMA (c). These images were taken following nuclear matrix preparation. Alterations in NuMA distribution between non-malignant and malignant cells are not accompanied by detectable changes in the level of expression of the protein, as shown by Western blot analysis (e).

NuMA distribution in tumor T4-2 cells and non-malignant S1-50 cells grown in 3D-rBM culture As shown in FIG. 6, at day 10 of 3D culture T4-2 cells form disorganized clusters in which nuclear NuMA is diffusely distributed (d), whereas NuMA is concentrated into enlarged foci at the periphery of the nuclei of non-malignant cells that have undergone acinar morphogenesis (c). Moreover, it is possible to follow the stepwise reorganization of NuMA in non-malignant cells up to day 10: in early culture (day 3), cells are proliferating and display a diffuse distribution pattern for NuMA (a), as the cells arrest growth (day 5–6) they show a patchier distribution for NuMA (b). These images were taken following nuclear matrix preparation. However the pattern of NuMA organization is similar in intact cells. The fact that the various patterns displayed by NuMA in intact cells are also seen in nuclear matrices, indicates that the supramolecular organization of NuMA distribution is somehow linked to the nuclear skeleton. Alterations in NuMA distribution between non-malignant and malignant cells are not accompanied by detectable changes in the level of expression of the protein, as shown by Western blot analysis (e). Arrows indicate individual nuclei.

At day 10 of 3D culture T4-2 cells form disorganized clusters in which nuclear NuMA is diffusely distributed (d), whereas NuMA is concentrated into enlarged foci at the periphery of the nuclei of non-malignant cells that have undergone acinar morphogenesis (b). Moreover, it is possible to follow the stepwise reorganization of NuMA in non-malignant cells up to day 10: in early culture (day 3), cells are proliferating and display a diffuse distribution pattern for NuMA (a), as the cells arrest growth (day 5–6) they show a patchier distribution for NuMA (c). These images were taken following nuclear matrix preparation. However the pattern of NuMA organization is similar to that found in intact cells. The fact that the various patterns displayed by NuMA in intact cells are also seen in nuclear matrices, indicates that the supramolecular organization of NuMA distribution is somehow linked to the nuclear skeleton. In addition, EM analysis shows that the biggest NuMA foci seen in nuclear matrix preparation of S1-50 cells corresponds to a location in interchromatin granule-like clusters, whereas NuMA is everywhere in the highly altered nuclear remnant of tumor T4-2 cells (not shown). Alterations in NuMA distribution between non-malignant and malignant cells are not accompanied by detectable changes in the level of expression of the protein, as shown by Western blot analysis (e).

Example 5

Modification of the behavior of non-malignant and malignant cells is accompanied by alteration in NuMA distribution.

Figure 7:
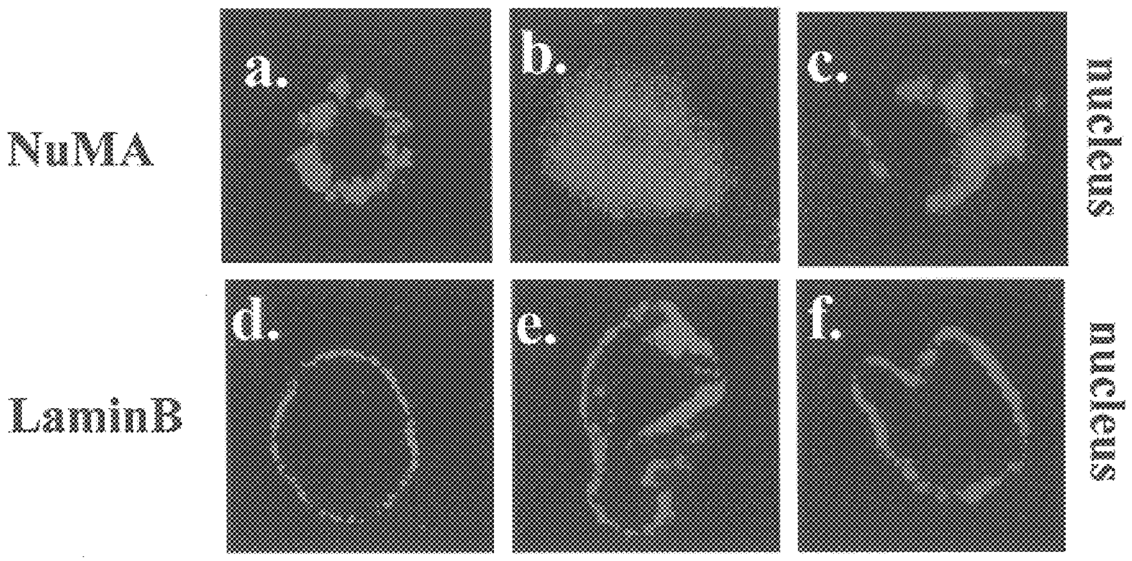
FIG. 7. (*a–f*)Distribution of NuMA in revertant T4-2 cells (RT4-2). Immunostaining of nuclear matrix preparation with NuMA antibody shows that NuMA is organized in large and peripheral foci in the nuclei of revertant cells (c), a distribution which is comparable to what is observed in S1-50 cells (a) but not in T4-2 tumor cells (b) in the same culture conditions. Immunostaining with lamin B antibody shows that revertant T4-2 cells keep a twisted nuclear shape (f) comparable to what is seen in control T4-2 tumor cells (e) whereas S 1-50 cells have a regular nuclear limit (d).

Tumor cells treated in 3D culture with either beta-i integrin blocking antibodies or tyrphostin form growth-arrested and organized acini. In FIG. 7, Tumor cells treated in 3D culture with either beta-1 integrin blocking antibodies or tyrphostin form growth-arrested and organized acini. Immunostaining of nuclear matrix preparation with NuMA antibody shows that NuMA is organized in large and peripheral foci in the nuclei of revertant cells (c), a distribution which is comparable to what is observed in S1-50 cells (a) but not in T4-2 tumor cells (b) in the same culture conditions. The same kind of reorganization is seen in intact cells (see FIG. 8). Immunostaining with lamin B antibody shows that revertant T4-2 cells keep a twisted nuclear shape (f) comparable to what is seen in control T4-2 tumor cells (e) whereas S1-50 cells have a regular nuclear limit (d). Therefore alteration of NuMA distribution is a good indicator of tumor cell reversion compared to changes in nuclear shape.

Iimmunostaining of nuclear matrix preparation with NuMA antibody shows that NuMA is organized in large and peripheral foci in the nuclei of revertant cells (c), a distribution which is comparable to what is observed in S1-50 cells (a) but not in T4-2 tumor cells (b) in the same culture conditions. The same kind of reorganization is seen in intact cells (see FIG. 8). Immunostaining with lamin B antibody shows that revertant T4-2 cells keep a twisted nuclear shape (f) comparable to what is seen in control T4-2 tumor cells (e) whereas S 1-50 cells have a regular nuclear limit (d). Therefore alteration of NuMA distribution is a good indicator of tumor cell reversion compared to changes in nuclear shape.

Introduction of NuMA antibodies in the nucleus of acinar RT4-2 cells leads to the degradation of the basement membrane in proportions similar to what was observed with S1-50 cells (see Example 3): 40% of acini show an incomplete BM in antibody-treated RT4-2 cells, whereas only 5% of acini show an incomplete BM in control immunoglobulins treated RT4-2 cells (not shown). This indicates that the relationship between NuMA organization and BM organization is re-established upon phenotypic reversion of T4-2 cells.

Figure 8:
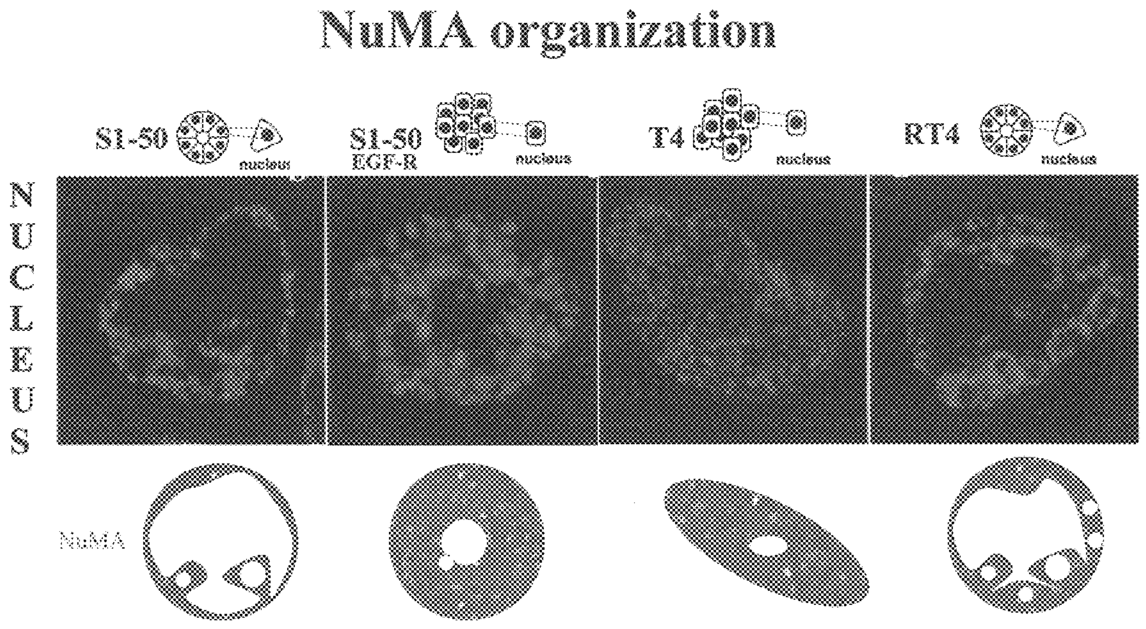
FIG. 8. (*a–f*) High magnification of NuMA distribution in S1-50, S1-50 EGFR, T4-2, and RT4-2 nuclei after 10 days of 3D culture. Nuclei of of S1-50 and RT4-2 cells which undergo acinar morphogenesis (a, d) and nuclei of S 1-EGFR and T4-2 cells which do not undergo acinar morphogenesis (b, c) and keep proliferating were stained with anti-NuMA antibody. NuMA is clearly peripheral in the nuclei of S1-50 and RT4-2 acinar cells and the foci-like organization appears to be due to the distribution of NuMA into intricate circles (a and d), while NuMA remains diffusely distributed in T4 and S1-EGFR cells. Only one nucleus is shown per image.

In order to obtain a better idea of NuMA distribution in the nucleus, we used a LEICA® confocal microscope which enables to visualize single nuclei at high magnification without losing resolution (FIG. 8). In FIG. 8, in order to obtain a better idea of NuMA distribution in the nucleus, we used a LEICA® confocal microscope which enables one to visualize single nuclei at high magnification without losing resolution. In addition to RT4 cells, S 1-50 cells which have been transfected with EGFR (S1-EGFR) have been included in the experiment. When cultured in 3D, S1-EGFR do not growth arrest and form large, slow growing cell clusters that are delineated by a basement membrane (as visualized using collagen IV staining).

Nuclei of S1-50 and RT4-2 cells which undergo acinar morphogenesis (a, d) and nuclei of S1-EGFR and T4-2 cells which do not undergo acinar morphogenesis (b,c) and keep proliferating were stained with anti-NuMA antibody. NuMA is clearly peripheral in the nuclei of S1-50 and RT4-2 acinar cells and the foci-like organization appears to be due to the distribution of NuMA into intricate circles (a and d), while NuMA remains diffusely distributed in T4 and S1-EGFR cells. Only one nucleus is shown per image.

In addition to RT4 cells, S1-50 cells which have been transfected with EGFR (S1-EGFR) have been included in the experiment. When cultured in 3D, S1-EGFR do not growth arrest and form large, slow growing cell clusters that are delineated by a basement membrane (as visualized using collagen IV staining).

Nuclei of S1-50 and RT4-2 cells which undergo acinar morphogenesis (a, d) and nuclei of S1-EGFR and T4-2 cells which do not undergo acinar morphogenesis (b,c) and keep proliferating were stained with anti-NuMA antibody. NuMA is clearly peripheral in the nuclei of S 1-50 and RT4-2 acinar cells and the foci-like organization appears to be due to the distribution of NuMA into intricate circles (a and d), while NuMA remains diffusely distributed in T4 and S1-EGFR cells. Only one nucleus is shown per image.

In addition, introduction of anti-NuMA antibody in S1-EGFR cells after 10 days in 3D cultures does not induce the degradation of collagen IV as opposed to what has been observed for S1-50 and RT4-2 cells, indicating that the connection between the basement membrane and NuMA is lost in S1-EGFR cells.

Example 6

Mathematical measurement of NuMA distribution demonstrates a significant difference between proliferating S1-50 cells and proliferating T4-2 cells.

The mathematical modeling of the measurement of punctateness is shown in FIG. 9. FIG. 9 shows the difference in the punctateness of NuMA staining between proliferating non- malignant and malignant cells cultured in 3D. Proliferating non-malignant S1-50 cells and malignant T4-2 cells (day 3 of 3D culture) were immunostained with anti-NuMA antibody. No significant difference in the staining pattern of NuMA could be detected by direct visualization of an S1-50 (a) or T4-2 (b) nucleus. However, the measurement of the punctateness of the staining revealed a significant difference in NuMA distribution between non-malignant and malignant cells, as shown by the higher level of contrast for NuMA staining in S1-50 cells compared to T4-2 cells. The histogram shows the results calculated for the fourth blurring step. It is therefore possible to discriminate between non-malignant and malignant cells, even if they are all proliferating by measuring the degree of punctateness of NuMA staining. In addition, EM analysis shows that the biggest NuMA foci seen in nuclear matrix preparation correspond to a location in interchromatin granule-like clusters whereas NuMA is everywhere in the highly altered nuclear remnant of tumor T4-2 cells (not shown).

Introduction of NuMA antibodies in the nucleus of acinar RT4-2 cells leads to the degradation of the basement membrane in proportions similar to what was observed with S1-50 cells: 40% of acini show an incomplete BM in antibody-treated RT4-2 cells, whereas only 5% of acini show an incomplete BM in control immunoglobulins treated RT4-2 cells (not shown). This indicates that the relationship between NuMA organization and BM organization is re-established upon phenotypic reversion of T4-2 cells.

In addition, introduction of anti-NuMA antibody in S1-EGFR cells after 10 days in 3D cultures does not induce the degradation of collagen IV as opposed to what has been observed for S1-50 and RT4-2 cells, indicating that the connection between the basement membrane and NuMA is lost in S1- EGFR cells. An algorithm was developed to measure the punctateness of staining patterns for the analysis of NuMA organization. A diffuse staining (fine pattern) blurred with defmed blur coefficients rapidly loses contrast (a, b, c) whereas a punctate staining (coarse pattern) blurred with the same coefficient loses contrast more gradually (d, e, f). The degree of contrast plotted in function of the blur factor gives a curve, the slope of which is steeper for a more diffuse staining. As a result, the curve drawn from a diffuse staining is below the curve drawn from a coarse staining (right panel). It was calculated that the fourth level of blurring on the scale used is sufficient to indicate if there is a significant difference between two staining patterns. All measurements are automatically normalized for background and staining intensity, and for nuclear volume.

An algorithm was developed to measure the punctateness of staining patterns for the analysis of NuMA organization. A diffuse staining (fine pattern) blurred with defined blur coefficients rapidly loses contrast (a, b, c) whereas a punctate staining (coarse pattern) blurred with the same coefficients loses contrast more gradually (d, e, f). The degree of contrast plotted in function of the blur factor gives a curve, the slope of which is steeper for a more diffuse staining. As a result, the curve drawn from a diffuse staining is below the curve drawn from a coarse staining (right panel). It was calculated that the fourth level of blurring on the scale used is sufficient to indicate if there is a significant difference between two staining patterns. All measurements are automatically normalized for background and staining intensity, and for nuclear volume.

As shown in Example 2, NuMA distribution looks more aggregated when S1-50 cells are growth-arrested compared to proliferation. As an indication of the usefulness of the algorithm to measure subtle differences in NuMA distribution, we recorded and tested images of NuMA staining in proliferating and growth-arrested cells. Topro-3 (Molecular Probes, Inc.) was used as a counterstaining for DNA which permitted the nuclear segmentation and the reconstruction of the entire nuclear volume. Calculations clearly indicated that NuMA staining is significantly more punctate (or less diffuse) in the nucleus of growth-arrested cells compared to proliferating cells, as shown by the higher level of contrast for NuMA staining in growth-arrested cells.

Hence data is presented corroborating the difference in NuMA distribution directly seen with the microscope. The histogram shows the results calculated for the fourth blurring step.

Figure 11:
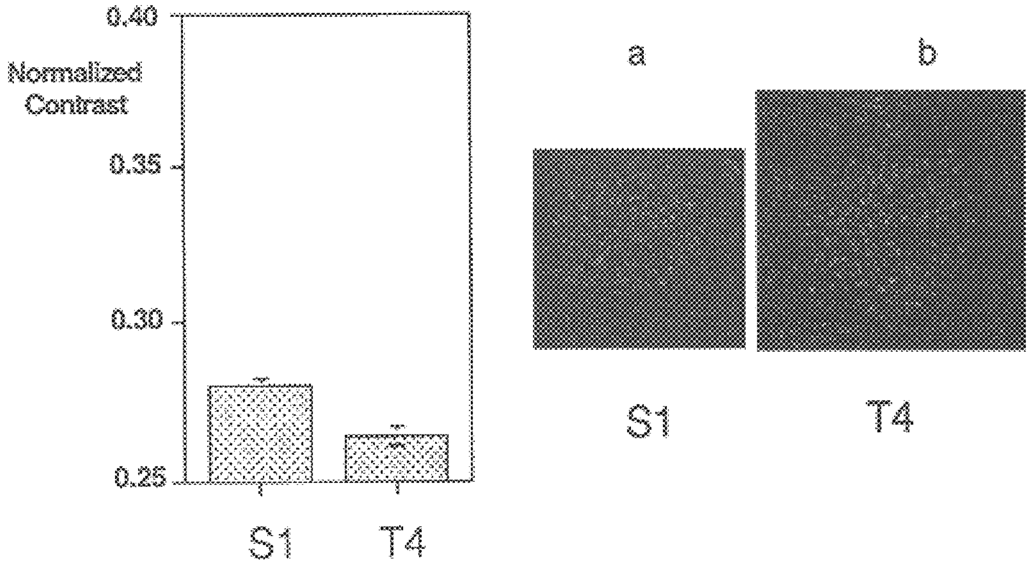
FIG. 11. Difference in the punctateness of NuMA staining between proliferating non-malignant and malignant cells cultured as monolayers (2D). Proliferating non-malignant S1-50 cells and malignant T4-2 cells were immunostained with anti-NuMA antibody. No significant difference in the staining pattern of NuMA could be detected by direct visualization of an S1-50 (a) or T4-2 (b) nucleus. However, the measurement of the punctateness of the staining revealed a significant difference in NuMA distribution between non-malignant and malignant cells, as shown by the higher level of contrast for NuMA staining in S1-50 cells compared to T4-2 cells. The histogram shows the results calculated for the fourth blurring step. Analysis of the levels and distribution of proliferation markers Rb, Ki-67/PCNA and cyclin D1 in proliferating S 1-50 and T4-2 cells revealed no detectable differences, as shown respectively by western blot analysis and immunostaining (not shown). Ki67 indicates that the cells are in the cell cycle (+). n is the number of nuclei analyzed.
Figure 12:
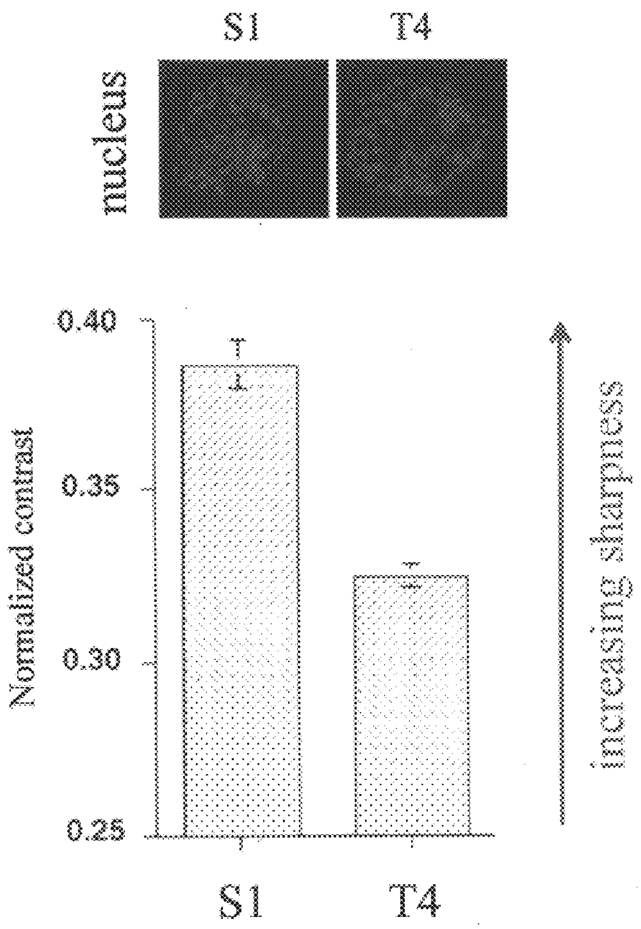
FIG. 12. Differences in the punctateness of NuMA staining between proliferating non-malignant and malignant cells cultured in 3D BM. Proliferating non-malignant S1-50 cells and malignant T4-2 cells (day 3 of 3D culture) were immunostained with anti-NuMA antibody. No significant difference in the staining pattern of NuMA could be detected by direct visualization of an S1-50 or T4-2 nucleus. However, the measurement of the punctateness of the staining revealed a significant difference in NuMA distribution between malignant and non-malignant cells, as shown by the higher level of contrast for NuMA staining in S 1-50 cells compared to T4-2 cells. The histogram shows the results calculated for the fourth blurring step. It is therefore possible to discriminate between non-malignant and malignant cells, even if they are all proliferating, by measuring the degree of punctateness of NuMA staining.

When proliferating non-malignant S1-50 cells, and malignant T4-2 cells cultured in 2D were immunostained with anti-NuMA antibody, no significant difference in the staining pattern of NuMA could be detected by direct visualization of an S1-50 (a) or T4-2 (b) nucleus (FIG. 11).

However, the measurement of the punctateness of the staining revealed a significant difference in NuMA distribution between non-malignant and malignant cells, as shown by the higher level of contrast for NuMA staining in S1-50 cells compared to T4-2 cells. The histogram shows the results calculated for the fourth blurring step. Analysis of the levels and distribution of proliferation markers Rb, Ki-67/PCNA and cyclin D1 in proliferating S1-50 and T4-2 cells revealed no detectable differences, as shown respectively by western blot analysis and immunostaining.

When proliferating non-malignant S1-50 cells and malignant T4-2 cells, at day 3 of 3D culture, were immunostained with anti-NuMA antibody. No significant difference in the staining pattern of NuMA could be detected by direct visualization of an S1-50 or T4-2 nucleus. However, the measurement of the punctateness of the staining revealed a significant difference in NuMA distribution between malignant and non-malignant cells, as shown by the higher level of contrast for NuMA staining in S1-50 cells compared to T4-2 cells. The histogram shows the results calculated for the fourth blurring step. It is therefore possible to discriminate between non-malignant and malignant cells, even if they are all proliferating, by measuring the degree of punctateness of NuMA staining.

Example 7

NuMA is a shuttling protein

The experiments described in Example 3 used cells permeabilized in vivo and subsequent treatment with NuMA antibodies introduced in the culture medium. The antibodies will penetrate into the cytoplasm thanks to the permeabilization treatment. However, in order to reach the nucleus the antibodies need to be translocated through the nucleopores. This is only possible if they are carried through the pores. Logically these antibodies are most likely to be carried by NuMA, the protein they are targeted to. Translocation of anti-NuMA antibody to the nucleus was rapid for both antibodies directed against the C-terminus and the N-terminus of NuMA protein. After a couple of days, the antibodies directed against the N-terminus of NuMA protein were found in the cytoplasm, indicating that they had translocated back from the nucleus to the cytoplasm. Such translocation is usually thought to happen by piggy-backing with the protein the antibodies are targeted to (in this case, NuMA). These data indicate that NuMA may be constantly shuttling in and out of the nucleus. Experiments using antibody injection were utilized already to demonstrate the shuttling of other proteins like the CMS protein zyxin.

To confirm that NuMA is a shuttling protein we have treated proliferating S1 cells cultured either in 2D or in 3D with 5 microM of actinomycin D. Actinomycin D has been shown to inhibit the shuttling of proteins. This results usually in the accumulation of the shuttling protein in the cytoplasm. In S1 cells cultured in 3D, actinomycin treatment induced the accumulation of NuMA in the cytoplasm of the cells (see FIG. 13A). Interestingly, in S1 cells cultured in 2D, actinomycin treatment induced the appearance of tracks of NuMA proteins within the cell nucleus and the accumulation of NuMA in the nucleus. Both results indicate that NuMA shuttles, however, the discrepancy between the effects obtained in the two types of culture suggest that NuMA shuttling is differently regulated in 3D cultures compared to 2 D cultures.

Heterokaryon fusion experiments were also performed. For these studies S1-50 or T4-2 cells were fused with mouse 3T3 cells. The heterokaryons were immunostained with an antibody that is specific for the human form of NuMA and doesn't recognize the mouse form (clone 107.7 from Matritech). In a number of cases both the human (S1 or T4) and mouse nuclei were stained within the heterokaryon indicating that NuMA had shuttled between the two nuclei. This type of experiment is considered as the ultimate demonstration that a protein shuttles between the cytoplasmic and the nuclear compartments.

Figure 13:
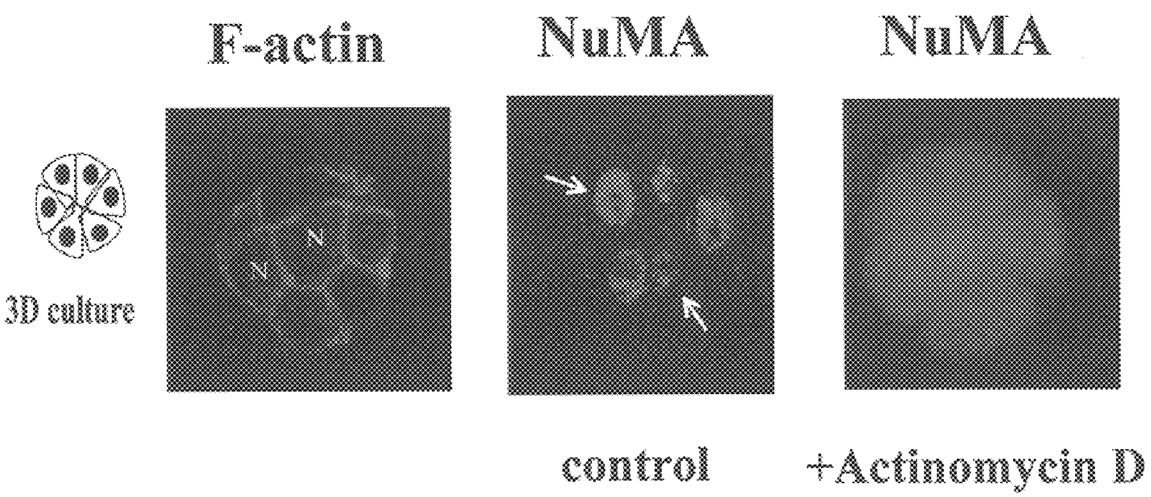
FIG. 13 (A) (*a–c*). Effect of actinomycin D on NuMA compartmentalization. Confocal fluorescence images (0.2μ optical sections) of F-actin (a) and NuMA (b,c) in early 3D cultures of human mammary epithelial cells S 1-50. F-actin staining indicates the boundaries of cells inside the 3D cluster (a; black holes represent the location of nuclei: N). Control: NuMA is localized in the nuclei of cells (b; nuclei indicated by arrows). Treatment with actinomycin D (AD) an inhibitor of transcription which has been shown to prevent the nuclear import of proteins: after a five hour treatment with AD (5 μg/ml), NuMA is found in both cytoplasmic and nuclear compartments, as indicated by a diffuse staining in the entire cell cluster (c).
Figure 13:
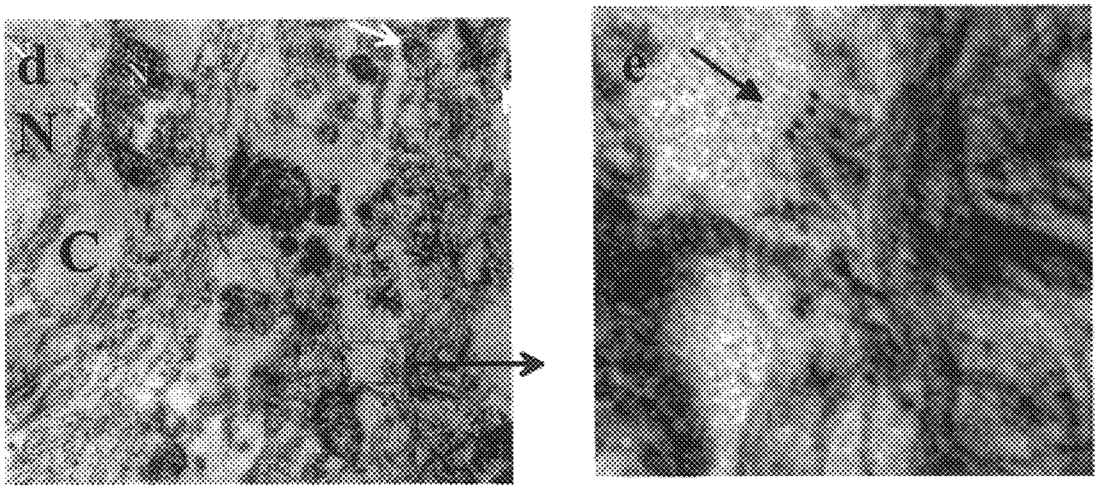

Finally, in order to image NuMA in the cytoplasmic compartment, we performed immunogold labeling with NuMA antibody and observed thin cell sections in electron microscopy. This high resolution microscopy revealed the presence of NuMA associated with cytoskeleton fibers (FIG. 13 B). This observation was confirmed with the soft X-ray microscopy in which cells are non sectioned and hydrated, thus ruling out the possibility of artifactual staining due to dehydration in electron microscopy.

Conclusion

According to the present invention, the localization of the nuclear structural protein NuMA can be used to identify different cellular behaviors (a) and to discriminate between non-malignant and malignant cells (b). For application (a) the technique encompasses immunostaining of 2D cell cultures, 3D cell cultures and tissue sections obtained from reduction tissueplasty and biopsies. For application (b) the technique encompasses immunostaining of 2D cell cultures, 3D cell cultures and tissue sections obtained from reduction tissueplasty and biopsies. It also requires the use of the punctateness algorithm.

Application (a): We use a simple and classical immunostaining technique in order to visualize nuclear structural proteins. This includes either sample fixation in methanol/acetone (1:1) at −20 deg. C for 10 minutes and further staining or a five-minute triton extraction followed by fixation in paraformaldehyde and further staining. We recommend the use of an antibody which recognizes the C-terminus of NuMA in order to visualize the complete panel of NuMA distribution patterns.

Suitable antibodies specific to NuMA may be made by conventional monoclonal or polyclonal techniques. Based on our work and other data present in the literature, it is possible to identify cells in mitosis, proliferating, growth-arrested, differentiated and dying, according to the pattern of NuMA distribution (see scheme: FIG. 14). NuMA staining will enable the identification of proliferating cells, as shown by a diffuse pattern within the nucleus, and mitosis, as shown by the localization of NuMA to the pole of the mitotic spindle. It is also possible to recognize growth-arrested cells, as shown by the patchier distribution of NuMA within the nucleus, although the use of the punctateness algorithm may be easier to apply here for non trained individuals. Cells undergoing cell death by apoptosis show a NuMA staining concentrated in one large foci in the center of the nucleus. Finally, cellular differentiation resembling the state of differentiation observed in mammary tissues can be recognized by the formation of enlarged and peripheral NuMA foci within the nucleus. The latter may be restricted to mammary epithelial cells until further analysis of other cell types, while the other distribution patterns may be used in many different cell and tissue types since NuMA as been shown to be present in numerous cell lines. Identification of the various types of NuMA distribution could be used for instance in the course of an experiment in cell culture or to assess the number of actively proliferating cells or dying cells in a tissue. This could be done to compare control and drug-treated cells or tissues, and in any other studies which involve alteration of the cellular behavior. The use of NuMA to discriminate between different cell behaviors could be applied for both non-malignant and malignant cells.

Application (b): Although tumor cells are expected to mainly present a diffuse staining pattern of NuMA within the nucleus easily distinguishable from the patchier or peripheral foci-like staining in respectively growth-arrested or differentiated cells, it is also possible that non-malignant cells be proliferating and show the same diffuse staining as tumor cells. In this case, our data show that we can discriminate between proliferating non-malignant cells and proliferating malignant cells using the punctateness algorithm. Non-malignant cells will show a higher degree of punctateness (FIG. 14). To the best of our knowledge this is the first demonstration of an assay that permits the discrimination between malignant and non-malignant cells both proliferating, and studied in the same experiment. Using this technique we can say that the more diffuse (or the less punctate) NuMA staining in a population of cells, the more aggressive the cells. It is envisioned that the study of many samples of proliferation disorders may enable us, in the long term, to define absolute range of numbers for NuMA punctateness that would permit the identification of single tumor cells within a sample.

Another example of redistribution of nuclear structural proteins within the cell nucleus upon development of malignancy has been shown for the PML protein in certain types of leukemias. However, so far this alteration cannot be applied for other tissues. For instance, in our studies with mammary epithelial cells, the PML protein shows no significant difference in its distribution between differentiated cells and tumor cells. However our results and results from others show that the distribution of certain splicing factors may be used to discriminate differentiated cells from non differentiated cells. Our preliminary results also suggest that alteration of the distribution of nuclear proteins like Rb and telomere-binding protein Tin2 may be used to identify different cellular phenotypes. Other proteins to investigate may be TRF1, Ku and transcription factors such as oct1.

The invention described herein is described in considerable detail to provide those skilled in the art with the information needed to apply the novel principles and to construct and use this inventive technology. However, it is to be understood that the invention can be carried out using different microscopic equipment and materials, and that various modifications both as to the equipment details and operational procedures can be made without departing from the scope of the invention itself.

REFERENCES

1. Berezney, R. & Coffey D. S. (1974) *Biochem. Biophys. Res. Commun.* 60, 1410–1417.

b 2.Nickerson, J. A., Blencowe, B. J. & Penman, S. (1995) *Int. Rev. Cytol.* 162A, 67–123.

3. Nickerson, J. A., Krockmalnic, G., Van, K. M. & Penman, S. (1997) *Proc. Natl. Acad Sci. USA* 94, 4446–4450.

4. Odgren, P. R., Harvie, L. W. & Fey, E. G. (1996) *Proteins* 24,467–484.

5. Mancini, M. A., Shan, B., Nickerson, J. A., Penman S. & Lee, W-H. (1994). *Proc.Natl.Acad.Sci. USA* 91, 418–422.

5. van Wijnen, A. J., Bidwell, J. P., Fey, E. G., Penman, S., Lian, J. B., Stein, J. & Stein, G. S. (1993) *Biochem.* 32, 8397–8402.

7. Nardozza, T. A., Quigley, M. M. & Getzenberg, R. H. (1996). *J Cell Biochem.* 61, 467–477.

8. Antoniou, M., Carmo-Fonseca, M., Ferreira, J. & Lamond, A. I. (1993) *J Cell Biol.* 123, 1055–1068.

6. Sahlas, D. J., Milankov, K., Park, P. C. & De Boni, U. (1993) *J Cell Sci.* 105, 347–357.

7. Misteli, T., Caceres, J. F. & Spector, D. L. (1997) *Nature* 387. 523–527.

8. Singer, R. H & Green, M. R. (1997). *Cell* 91, 291–294.

9. Briand, P., Petersen, O. W. & Van Deurs, B. (1987) In Vitro *Cell. Dev. Biol.* 23, 181–188.

10. Petersen, O. W., Rønnov-Jessen L., Howlett, A.R. & Bissell, M.J. (1992) *Proc. Natl. Acad Sci.* (JSA) 89, 9064–9068.

11. Gerace, L., Comeau, C. & Benson, M. (1984) *J. Cell Sci. Suppl.* 1, 137–160.

12. Lydersen, B. & Pettijohn, D. (1980) *Cell* 22, 489–499.

13. Blencowe, B. J., Issner R., Nickerson, J. A., & Sharp P. A. (1998) *Genes & Dev.* 12, 996–1009.

14. Bissell, M. J., Hall, H. G. & Parry, G. (1982)*J. Theor. Biol.* 99, 31–68.

15. Weaver, V. M., Petersen, O. W., Wang F., Larabell, C. A., Briand, P., Damsky, C. & Bissell, M. J. (1997)*J. Cell Biol.* 137, 231–245.

16. Myers, C. A., Schmidhauser, C., Mellentin-Michelotti, J., Fragoso, G., Roskelley, C. D., Casperson, G., Mossi, R., Pujuguet, P., Hager G. & Bissell, M. J. (1998) *Mol. Cell. Biol.* 18, 2184–2195.

17. He, D., Nickerson, J. A. & Penman, S. (1990)*J.Cell Biol.* 110, 569–580.

18. Merdes, A. & Cleveland, D. W. (1998)*J.Cell Sci.* 111, 71–79.

19. Howlett, A. R., Bailey, N., Damsky, C., Petersen, O. W. & Bissell, M.J. (1995) *J. Cell Sci.* 108, 1945–1957.

20. Pazin, M. J. & Kadonaga, J. T. (1997) Cell 89, 325–328.

21. Compton, D. A. & Cleveland, D. W. (1994) Curr.Opin-.Cell Biol. 6, 343–346.

22. Weaver, V. M., Carson, C. E., Walker, P. R., Chaly, N., Lach, B., Raymond,Y., Brown, D.L. & Sikorska, M. (1996) *J. Cell Sci.* 109, 45–56.

23. Grobelny, D., Poncz, L. & Galardy, R. E. (1992) *Biochem.* 31, 7152–7154.

24. Dhawan, J. & Farmer, S. R. (1990) *J. Biol. Chem.* 266, 8470–8475.

25. Streuli, C. H., Bailey, N. & Bissell, M. J. (1991)*J. Cell Biol.* 115, 1383–1395.

26. Boudreau, N., Sympson, C.J., Werb, Z. & Bissell, M. J. (1995) *Science* 267, 891–893.

---

We claim:

1. A method for distinguishing malignant and proliferating non-malignant cells, comprising:

(a) supplying a sample of intact mammalian cells;

(b) staining specifically Nuclear Mitotic Apparatus (NUMA) protein in said cells;

(c) imaging said cells to determine the three dimensional pattern of labeled NUMA protein within nuclei of said cells; and (d) comparing the pattern of NUMA protein obtained in step (c) with known three dimensional pattern data from stained NUMA protein in malignant and proliferating non- malignant cells, whereby a lower degree of punctateness is correlated with malignancy.

2. The method of claim 1, wherein the imaging step is performed using a confocal microscope.

3. A method for distinguishing growth arrested, malignant and proliferating non-malignant cells, comprising:

(a) supplying a sample of intact mammalian cells;

(b) staining specifically Nuclear Mitotic Apparatus (NUMA) protein in said cells;

(c) imaging said cells to determine the three dimensional pattern of labeled NUMA protein within the cells; and (d) comparing the pattern of NUMA protein obtained in step (c) with known three dimensional pattern data from stained NUMA protein in malignant and proliferating non-malignant cells, whereby a lower degree of punctateness is correlated with malignancy and growth arrested cells correlate with the highest degree of NUMA protein concentration.

4. The method of claim 3, wherein the imaging step is performed using a confocal microscope.

* * * * *

SEQUENCE LISTING

```
<160> NUMBER OF SEQ ID NOS:  1

<210> SEQ ID NO 1
<211> LENGTH: 2101
<212> TYPE: PRT
<213> ORGANISM: Homo sapiens

<400> SEQUENCE: 1

Met Thr Leu His Ala Thr Arg Gly Ala Ala Leu Leu Ser Trp Val Asn
  1               5                  10                  15

Ser Leu His Val Ala Asp Pro Val Glu Ala Val Leu Gln Leu Gln Asp
             20                  25                  30

Cys Ser Ile Phe Ile Lys Ile Ile Asp Arg Ile His Gly Thr Glu Glu
         35                  40                  45

Gly Gln Gln Ile Leu Lys Gln Pro Val Ser Glu Arg Leu Asp Phe Val
     50                  55                  60

Cys Ser Phe Leu Gln Lys Asn Arg Lys His Pro Ser Ser Pro Glu Cys
 65                  70                  75                  80

Leu Val Ser Ala Gln Lys Val Leu Glu Gly Ser Glu Leu Glu Leu Ala
```

-continued

```
                85                  90                  95

Lys Met Thr Met Leu Leu Leu Tyr His Ser Thr Met Ser Ser Lys Ser
            100                 105                 110

Pro Arg Asp Trp Glu Gln Phe Glu Tyr Lys Ile Gln Ala Glu Leu Ala
        115                 120                 125

Val Ile Leu Lys Phe Val Leu Asp His Glu Asp Gly Leu Asn Leu Asn
    130                 135                 140

Glu Asp Leu Glu Asn Phe Leu Gln Lys Ala Pro Val Pro Ser Thr Cys
145                 150                 155                 160

Ser Ser Thr Phe Pro Glu Glu Leu Ser Pro Pro Ser His Gln Ala Lys
                165                 170                 175

Arg Glu Ile Arg Phe Leu Glu Leu Gln Lys Val Ala Ser Ser Ser Ser
            180                 185                 190

Gly Asn Asn Phe Leu Ser Gly Ser Pro Ala Ser Pro Met Gly Asp Ile
        195                 200                 205

Leu Gln Thr Pro Gln Phe Gln Met Arg Arg Leu Lys Lys Gln Leu Ala
    210                 215                 220

Asp Glu Arg Ser Asn Arg Asp Glu Leu Glu Leu Glu Leu Ala Glu Asn
225                 230                 235                 240

Arg Lys Leu Leu Thr Glu Lys Asp Ala Gln Ile Ala Met Met Gln Gln
                245                 250                 255

Arg Ile Asp Arg Leu Ala Leu Leu Asn Glu Lys Gln Ala Ala Ser Pro
            260                 265                 270

Leu Glu Pro Lys Glu Leu Glu Glu Leu Arg Asp Lys Asn Glu Ser Leu
        275                 280                 285

Thr Met Arg Leu His Glu Thr Leu Lys Gln Cys Gln Asp Leu Lys Thr
    290                 295                 300

Glu Lys Ser Gln Met Asp Arg Lys Ile Asn Gln Leu Ser Glu Glu Asn
305                 310                 315                 320

Gly Asp Leu Ser Phe Lys Leu Arg Glu Phe Ala Ser His Leu Gln Gln
                325                 330                 335

Leu Gln Asp Ala Leu Asn Glu Leu Thr Glu Glu His Ser Lys Ala Thr
            340                 345                 350

Gln Glu Trp Leu Glu Lys Gln Ala Gln Leu Glu Lys Glu Leu Ser Ala
        355                 360                 365

Ala Leu Gln Asp Lys Lys Cys Leu Glu Glu Lys Asn Glu Ile Leu Gln
    370                 375                 380

Gly Lys Leu Ser Gln Leu Glu Glu His Leu Ser Gln Leu Gln Asp Asn
385                 390                 395                 400

Pro Pro Gln Glu Lys Gly Glu Val Leu Gly Asp Val Leu Gln Leu Glu
                405                 410                 415

Thr Leu Lys Gln Glu Ala Ala Thr Leu Ala Ala Asn Asn Thr Gln Leu
            420                 425                 430

Gln Ala Arg Val Glu Met Leu Glu Thr Glu Arg Gly Gln Gln Glu Ala
        435                 440                 445

Lys Leu Leu Ala Glu Arg Gly His Phe Glu Glu Glu Lys Gln Gln Leu
    450                 455                 460

Ser Ser Leu Ile Thr Asp Leu Gln Ser Ser Ile Ser Asn Leu Ser Gln
465                 470                 475                 480

Ala Lys Glu Glu Leu Glu Gln Ala Ser Gln Ala His Gly Ala Arg Leu
                485                 490                 495

Thr Ala Gln Val Ala Ser Leu Thr Ser Glu Leu Thr Thr Leu Asn Ala
            500                 505                 510
```

-continued

```
Thr Ile Gln Gln Gln Asp Gln Glu Leu Ala Gly Leu Lys Gln Gln Ala
            515                 520                 525

Lys Glu Lys Gln Ala Gln Leu Ala Gln Thr Leu Gln Gln Gln Glu Gln
    530                 535                 540

Ala Ser Gln Gly Leu Arg His Gln Val Glu Gln Leu Ser Ser Ser Leu
545                 550                 555                 560

Lys Gln Lys Glu Gln Gln Leu Lys Glu Val Ala Glu Lys Gln Glu Ala
                565                 570                 575

Thr Arg Gln Asp His Ala Gln Gln Leu Ala Thr Ala Ala Glu Glu Arg
            580                 585                 590

Glu Ala Ser Leu Arg Glu Arg Asp Ala Ala Leu Lys Gln Leu Glu Ala
        595                 600                 605

Leu Glu Lys Glu Lys Ala Ala Lys Leu Glu Ile Leu Gln Gln Gln Leu
    610                 615                 620

Gln Val Ala Asn Glu Ala Arg Asp Ser Ala Gln Thr Ser Val Thr Gln
625                 630                 635                 640

Ala Gln Arg Glu Lys Ala Glu Leu Ser Arg Lys Val Glu Glu Leu Gln
                645                 650                 655

Ala Cys Val Glu Thr Ala Arg Gln Glu Gln His Glu Ala Gln Ala Gln
            660                 665                 670

Val Ala Glu Leu Glu Leu Gln Leu Arg Ser Glu Gln Gln Lys Ala Thr
        675                 680                 685

Glu Lys Glu Arg Val Ala Gln Glu Lys Asp Gln Leu Gln Glu Gln Leu
    690                 695                 700

Gln Ala Leu Lys Glu Ser Leu Lys Val Thr Lys Gly Ser Leu Glu Glu
705                 710                 715                 720

Glu Lys Arg Arg Ala Ala Asp Ala Leu Glu Glu Gln Gln Arg Cys Ile
                725                 730                 735

Ser Glu Leu Lys Ala Glu Thr Arg Ser Leu Val Glu Gln His Lys Arg
            740                 745                 750

Glu Arg Lys Glu Leu Glu Glu Glu Arg Ala Gly Arg Lys Gly Leu Glu
        755                 760                 765

Ala Arg Leu Leu Gln Leu Gly Glu Ala His Gln Ala Glu Thr Glu Val
    770                 775                 780

Leu Arg Arg Glu Leu Ala Glu Ala Met Ala Ala Gln His Thr Ala Glu
785                 790                 795                 800

Ser Glu Cys Glu Gln Leu Val Lys Glu Val Ala Ala Trp Arg Asp Gly
                805                 810                 815

Tyr Glu Asp Ser Gln Gln Glu Glu Ala Gln Tyr Gly Ala Met Phe Gln
            820                 825                 830

Glu Gln Leu Met Thr Leu Lys Glu Glu Cys Glu Lys Ala Arg Gln Glu
        835                 840                 845

Leu Gln Glu Ala Lys Glu Lys Val Ala Gly Ile Glu Ser His Ser Glu
    850                 855                 860

Leu Gln Ile Ser Arg Gln Gln Asn Lys Leu Ala Glu Leu His Ala Asn
865                 870                 875                 880

Leu Ala Arg Ala Leu Gln Gln Val Gln Glu Lys Glu Val Arg Ala Gln
                885                 890                 895

Lys Leu Ala Asp Asp Leu Ser Thr Leu Gln Glu Lys Met Ala Ala Thr
            900                 905                 910

Ser Lys Glu Val Ala Arg Leu Glu Thr Leu Val Arg Lys Ala Gly Glu
        915                 920                 925
```

-continued

```
Gln Gln Glu Thr Ala Ser Arg Glu Leu Val Lys Glu Pro Ala Arg Ala
    930                 935                 940

Gly Asp Arg Gln Pro Glu Trp Leu Glu Glu Gln Gln Gly Arg Gln Phe
945                 950                 955                 960

Cys Ser Thr Gln Ala Ala Leu Gln Ala Met Glu Arg Glu Ala Glu Gln
                965                 970                 975

Met Gly Asn Glu Leu Glu Arg Leu Arg Ala Ala Leu Met Glu Ser Gln
            980                 985                 990

Gly Gln Gln Gln Glu Glu Arg Gly Gln Gln Glu Arg Glu Val Ala Arg
        995                 1000                1005

Leu Thr Gln Glu Arg Gly Arg Ala Gln Ala Asp Leu Ala Leu Glu Lys
   1010                 1015                1020

Ala Ala Arg Ala Glu Leu Glu Met Arg Leu Gln Asn Ala Leu Asn Glu
1025                1030                1035                1040

Gln Arg Val Glu Phe Ala Thr Leu Gln Glu Ala Leu Ala His Ala Leu
                1045                1050                1055

Thr Glu Lys Glu Gly Lys Asp Gln Glu Leu Ala Lys Leu Arg Gly Leu
            1060                1065                1070

Glu Ala Ala Gln Ile Lys Glu Leu Glu Glu Leu Arg Gln Thr Val Lys
        1075                1080                1085

Gln Leu Lys Glu Gln Leu Ala Lys Lys Glu Lys Glu His Ala Ser Gly
   1090                 1095                1100

Ser Gly Ala Gln Ser Glu Ala Ala Gly Arg Thr Glu Pro Thr Gly Pro
1105                1110                1115                1120

Lys Leu Glu Ala Leu Arg Ala Glu Val Ser Lys Leu Glu Gln Gln Cys
                1125                1130                1135

Gln Lys Gln Gln Glu Gln Ala Asp Ser Leu Glu Arg Ser Leu Glu Ala
            1140                1145                1150

Glu Arg Ala Ser Arg Ala Glu Arg Asp Ser Ala Leu Glu Thr Leu Gln
        1155                1160                1165

Gly Gln Leu Glu Glu Lys Ala Gln Glu Leu Gly His Ser Gln Ser Ala
   1170                 1175                1180

Leu Ala Ser Ala Gln Arg Glu Leu Ala Ala Phe Arg Thr Lys Val Gln
1185                1190                1195                1200

Asp His Ser Lys Ala Glu Asp Glu Trp Lys Ala Gln Val Ala Arg Gly
                1205                1210                1215

Arg Gln Glu Ala Glu Arg Lys Asn Ser Leu Ile Ser Ser Leu Glu Glu
            1220                1225                1230

Glu Val Ser Ile Leu Asn Arg Gln Val Leu Glu Lys Glu Gly Glu Ser
        1235                1240                1245

Lys Glu Leu Lys Arg Leu Val Met Ala Glu Ser Glu Lys Ser Gln Lys
   1250                 1255                1260

Leu Glu Glu Ser Cys Ala Cys Cys Arg Gln Arg Gln Pro Ala Thr Val
1265                1270                1275                1280

Pro Glu Leu Gln Asn Ala Ala Leu Leu Cys Gly Arg Arg Cys Arg Ala
                1285                1290                1295

Ser Gly Arg Glu Ala Glu Lys Gln Arg Val Ala Ser Glu Asn Leu Arg
            1300                1305                1310

Gln Glu Leu Thr Ser Gln Ala Glu Arg Ala Glu Glu Leu Gly Gln Glu
        1315                1320                1325

Leu Lys Ala Trp Gln Glu Lys Phe Phe Gln Lys Glu Gln Ala Leu Ser
   1330                 1335                1340

Thr Leu Gln Leu Glu His Thr Ser Thr Gln Ala Leu Val Ser Glu Leu
```

-continued

```
1345                1350                1355                1360

Leu Pro Ala Lys His Leu Cys Gln Gln Leu Gln Ala Glu Gln Ala Ala
                1365                1370                1375

Ala Glu Lys Arg His Arg Glu Glu Leu Glu Gln Ser Lys Gln Ala Ala
            1380                1385                1390

Gly Gly Leu Arg Ala Glu Leu Leu Arg Ala Gln Arg Glu Leu Gly Glu
        1395                1400                1405

Leu Ile Pro Leu Arg Gln Lys Val Ala Glu Gln Glu Arg Thr Ala Gln
    1410                1415                1420

Gln Leu Arg Ala Glu Lys Ala Ser Tyr Ala Glu Gln Leu Ser Met Leu
1425                1430                1435                1440

Lys Lys Ala His Gly Leu Leu Ala Glu Glu Asn Arg Gly Leu Gly Glu
                1445                1450                1455

Arg Ala Asn Leu Gly Arg Gln Phe Leu Glu Val Glu Leu Asp Gln Ala
            1460                1465                1470

Arg Glu Lys Tyr Val Gln Glu Leu Ala Ala Val Arg Ala Asp Ala Glu
        1475                1480                1485

Thr Arg Leu Ala Glu Val Gln Arg Glu Ala Gln Ser Thr Ala Arg Glu
    1490                1495                1500

Leu Glu Val Met Thr Ala Lys Tyr Glu Gly Ala Lys Val Lys Val Leu
1505                1510                1515                1520

Glu Glu Arg Gln Arg Phe Gln Glu Glu Arg Gln Lys Leu Thr Ala Gln
                1525                1530                1535

Val Glu Glu Leu Ser Lys Lys Leu Ala Asp Ser Asp Gln Ala Ser Lys
            1540                1545                1550

Val Gln Gln Gln Lys Leu Lys Ala Val Gln Ala Gln Gly Gly Glu Ser
        1555                1560                1565

Gln Gln Glu Ala Gln Arg Phe Gln Ala Gln Leu Asn Glu Leu Gln Ala
    1570                1575                1580

Gln Leu Ser Gln Lys Glu Gln Ala Ala Glu His Tyr Lys Leu Gln Met
1585                1590                1595                1600

Glu Lys Ala Lys Thr His Tyr Asp Ala Lys Lys Gln Gln Asn Gln Glu
                1605                1610                1615

Leu Gln Glu Gln Leu Arg Ser Leu Glu Gln Leu Gln Lys Glu Asn Lys
            1620                1625                1630

Glu Leu Arg Ala Glu Ala Glu Arg Leu Gly His Glu Leu Gln Gln Ala
        1635                1640                1645

Gly Leu Lys Thr Lys Glu Ala Glu Gln Thr Cys Arg His Leu Thr Ala
    1650                1655                1660

Gln Val Arg Ser Leu Glu Ala Gln Val Ala His Ala Asp Gln Gln Leu
1665                1670                1675                1680

Arg Asp Leu Gly Lys Phe Gln Val Ala Thr Asp Ala Leu Lys Ser Arg
                1685                1690                1695

Glu Pro Gln Ala Lys Pro Gln Leu Asp Leu Ser Ile Asp Ser Leu Asp
            1700                1705                1710

Leu Ser Cys Glu Glu Gly Thr Pro Leu Ser Ile Thr Ser Lys Leu Pro
        1715                1720                1725

Arg Thr Gln Pro Asp Gly Thr Ser Val Pro Gly Glu Pro Ala Ser Pro
    1730                1735                1740

Ile Ser Gln Arg Leu Pro Pro Lys Val Glu Ser Leu Glu Ser Leu Tyr
1745                1750                1755                1760

Phe Thr Pro Ile Pro Ala Arg Ser Gln Ala Pro Leu Glu Ser Ser Leu
                1765                1770                1775
```

-continued

```
Asp Ser Leu Gly Asp Val Phe Leu Asp Ser Gly Arg Lys Thr Arg Ser
            1780                1785                1790

Ala Arg Arg Arg Thr Thr Gln Ile Ile Asn Ile Thr Met Thr Lys Lys
        1795                1800                1805

Leu Asp Val Glu Glu Pro Asp Ser Ala Asn Ser Ser Phe Tyr Ser Thr
    1810                1815                1820

Arg Ser Ala Pro Ala Ser Gln Ala Ser Leu Arg Ala Thr Ser Ser Thr
1825                1830                1835                1840

Gln Ser Leu Ala Arg Leu Gly Ser Pro Asp Tyr Gly Asn Ser Ala Leu
                1845                1850                1855

Leu Ser Leu Pro Gly Tyr Arg Pro Thr Thr Arg Ser Ser Ala Arg Arg
            1860                1865                1870

Ser Gln Ala Gly Val Ser Ser Gly Ala Pro Pro Gly Arg Asn Ser Phe
        1875                1880                1885

Tyr Met Gly Thr Cys Gln Asp Glu Pro Glu Gln Leu Asp Asp Trp Asn
    1890                1895                1900

Arg Ile Ala Glu Leu Gln Gln Arg Asn Arg Val Cys Pro Pro His Leu
1905                1910                1915                1920

Lys Thr Cys Tyr Pro Leu Glu Ser Arg Pro Ser Leu Ser Leu Gly Thr
                1925                1930                1935

Ile Thr Asp Glu Glu Met Lys Thr Gly Asp Pro Gln Glu Thr Leu Arg
            1940                1945                1950

Arg Ala Ser Met Gln Pro Ile Gln Ile Ala Glu Gly Thr Gly Ile Thr
        1955                1960                1965

Thr Arg Gln Gln Arg Lys Arg Val Ser Leu Glu Pro His Gln Gly Pro
    1970                1975                1980

Gly Thr Pro Glu Ser Lys Lys Ala Thr Ser Cys Phe Pro Arg Pro Met
1985                1990                1995                2000

Thr Pro Arg Asp Arg His Glu Gly Arg Lys Gln Ser Thr Thr Glu Ala
                2005                2010                2015

Gln Lys Lys Ala Ala Pro Ala Ser Thr Lys Gln Ala Asp Arg Arg Gln
            2020                2025                2030

Ser Met Ala Phe Ser Ile Leu Asn Thr Pro Lys Lys Leu Gly Asn Ser
        2035                2040                2045

Leu Leu Arg Arg Gly Ala Ser Lys Lys Ala Leu Ser Lys Ala Ser Pro
    2050                2055                2060

Asn Thr Arg Ser Gly Thr Arg Arg Ser Pro Arg Ile Ala Thr Thr Thr
2065                2070                2075                2080

Ala Ser Ala Ala Thr Ala Ala Ala Ile Gly Ala Thr Pro Arg Ala Lys
                2085                2090                2095

Gly Lys Ala Lys His
            2100
```